United States Patent
Badie

(10) Patent No.: US 9,320,540 B2
(45) Date of Patent: Apr. 26, 2016

(54) SURGICAL DEVICES AND RELATED METHODS THEREOF

(75) Inventor: Behnam Badie, LaCanada, CA (US)

(73) Assignee: MADISON SURGICAL DESIGNS, LLC, La Canada, CA (US)

( * ) Notice: Subject to any disclaimer, the term of this patent is extended or adjusted under 35 U.S.C. 154(b) by 1047 days.

(21) Appl. No.: 12/638,619

(22) Filed: Dec. 15, 2009

(65) Prior Publication Data

US 2010/0145330 A1   Jun. 10, 2010

Related U.S. Application Data

(63) Continuation-in-part of application No. 11/515,524, filed on Sep. 5, 2006, now abandoned.

(60) Provisional application No. 60/757,652, filed on Jan. 10, 2006, provisional application No. 60/713,639, filed on Sep. 2, 2005.

(51) Int. Cl.
| | |
|---|---|
| *A61B 18/14* | (2006.01) |
| *A61B 17/34* | (2006.01) |
| *A61B 17/3207* | (2006.01) |
| *A61B 18/00* | (2006.01) |
| *A61B 17/32* | (2006.01) |
| *A61B 17/3205* | (2006.01) |
| *A61B 18/20* | (2006.01) |
| *A61B 19/00* | (2006.01) |

(52) U.S. Cl.
CPC ....... *A61B 17/3421* (2013.01); *A61B 17/32002* (2013.01); *A61B 17/320725* (2013.01); *A61B 17/320016* (2013.01); *A61B 17/32056* (2013.01); *A61B 18/1402* (2013.01); *A61B 18/148* (2013.01); *A61B 18/20* (2013.01); *A61B 19/20* (2013.01); *A61B 2017/3443* (2013.01); *A61B 2017/3492* (2013.01); *A61B 2018/00267* (2013.01); *A61B 2018/00446* (2013.01); *A61B 2018/00595* (2013.01); *A61B 2018/00601* (2013.01); *A61B 2018/144* (2013.01); *A61B 2018/1407* (2013.01); *A61B 2019/208* (2013.01)

(58) Field of Classification Search
CPC .......... A61B 2018/00214; A61B 2018/00446; A61B 2018/00601; A61B 2018/1407; A61B 2018/00267; A61B 2018/144; A61B 2018/1475
USPC .............................................. 606/46–47, 113
See application file for complete search history.

(56) References Cited

U.S. PATENT DOCUMENTS

| | | | |
|---|---|---|---|
| 3,135,263 | A | 6/1964 | Connelley, Jr. |
| 4,487,600 | A | 12/1984 | Brownlie et al. |

(Continued)

*Primary Examiner* — Jaymi Della
(74) *Attorney, Agent, or Firm* — Kilpatrick Townsend & Stockton LLP

(57) ABSTRACT

Surgical devices and methods are configured to access areas of the brain while minimizing brain damage. A brain probe device for removing a lesion from a brain includes a cannula fixable to the skull to align the cannula with the lesion, a tubular stem within the cannula configured to be advanced to the lesion, and a rotatable cutting tube within the tubular stem. Expandable wire loops configured to cut tissue are attached to the distal end of the tubular stem. A loop expander and rotation motor mechanism is operably linked to the wire loops and configured to cause rotation and variable outward expansion of the wire loops. Tissue cut by the wire loops is removed through slots and a central lumen of the tubular stem. The cutting tube is rotatable to sever tissue drawn into the slots into smaller fragments that are removed through the central lumen via aspiration.

20 Claims, 18 Drawing Sheets

(56) References Cited

U.S. PATENT DOCUMENTS

| | | | |
|---|---|---|---|
| 5,030,201 A * | 7/1991 | Palestrant | 604/22 |
| 5,366,468 A | 11/1994 | Fucci et al. | |
| 5,794,626 A * | 8/1998 | Kieturakis | 600/567 |
| 6,032,673 A * | 3/2000 | Savage et al. | 128/898 |
| 6,743,245 B2 * | 6/2004 | Lobdell | 606/171 |
| 2002/0019597 A1 | 2/2002 | Dubrul et al. | |
| 2002/0022850 A1 * | 2/2002 | McGuckin, Jr. | 606/114 |
| 2002/0068879 A1 * | 6/2002 | Lubock et al. | 600/567 |
| 2002/0072688 A1 * | 6/2002 | Burbank et al. | 600/567 |
| 2002/0074005 A1 * | 6/2002 | Hogg et al. | 128/899 |
| 2004/0171967 A1 * | 9/2004 | Burbank et al. | 600/567 |

* cited by examiner

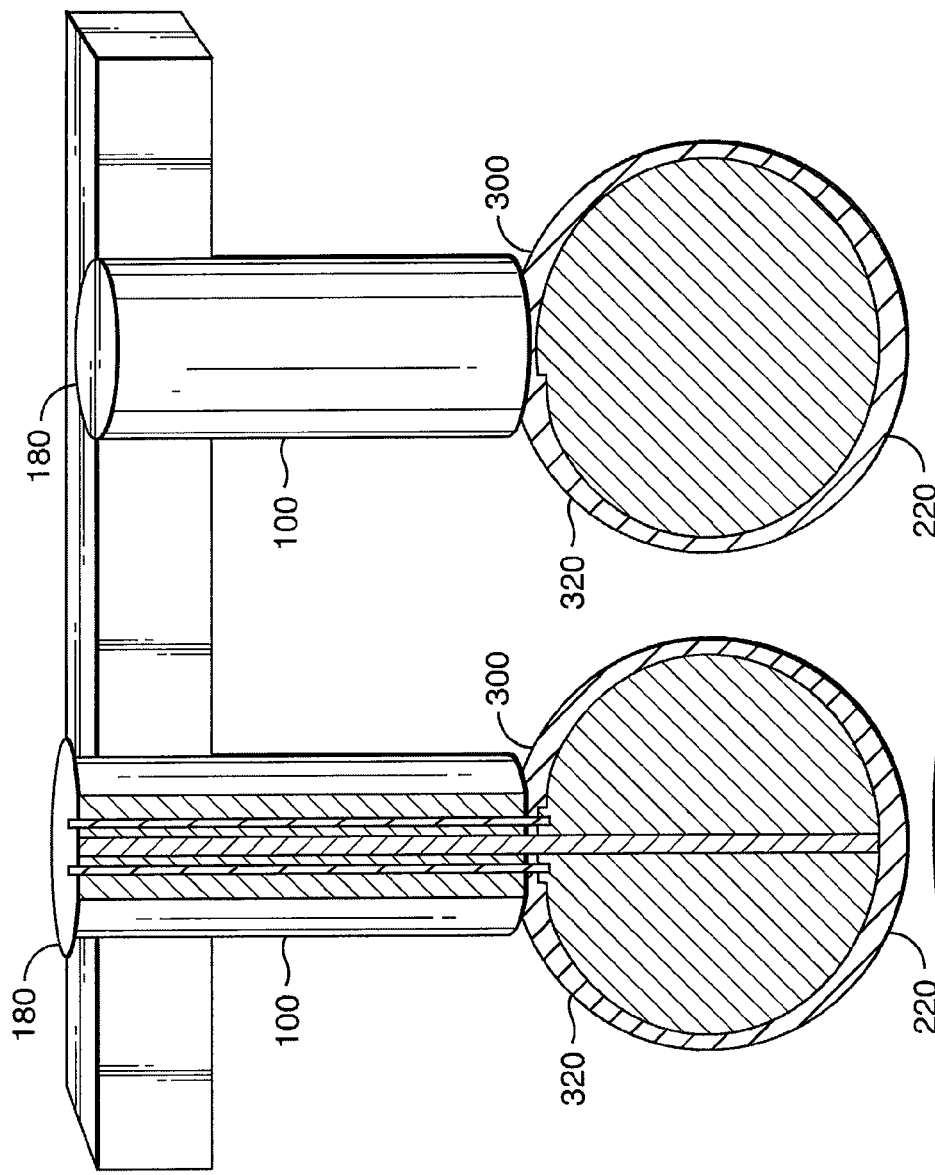

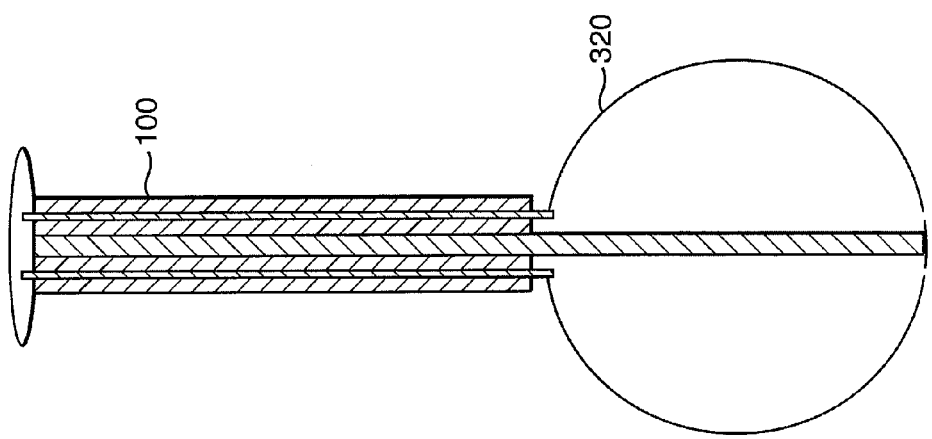
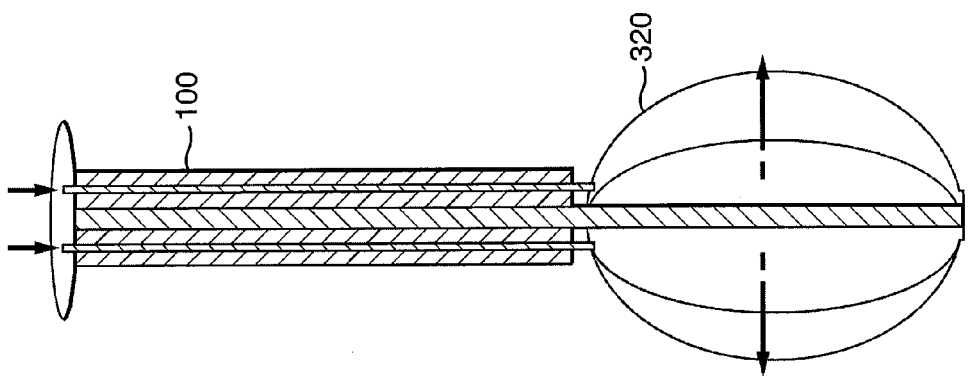
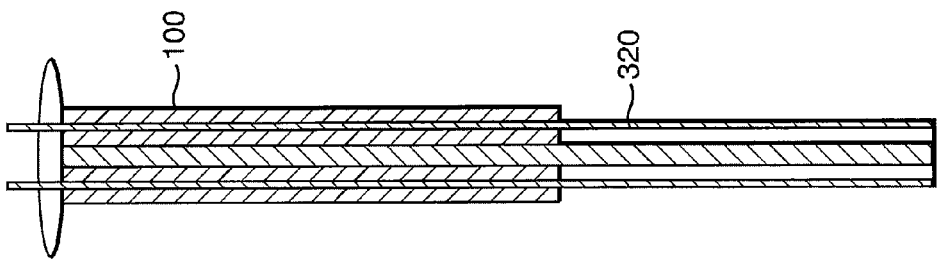
FIG. 6C
FIG. 6B
FIG. 6A

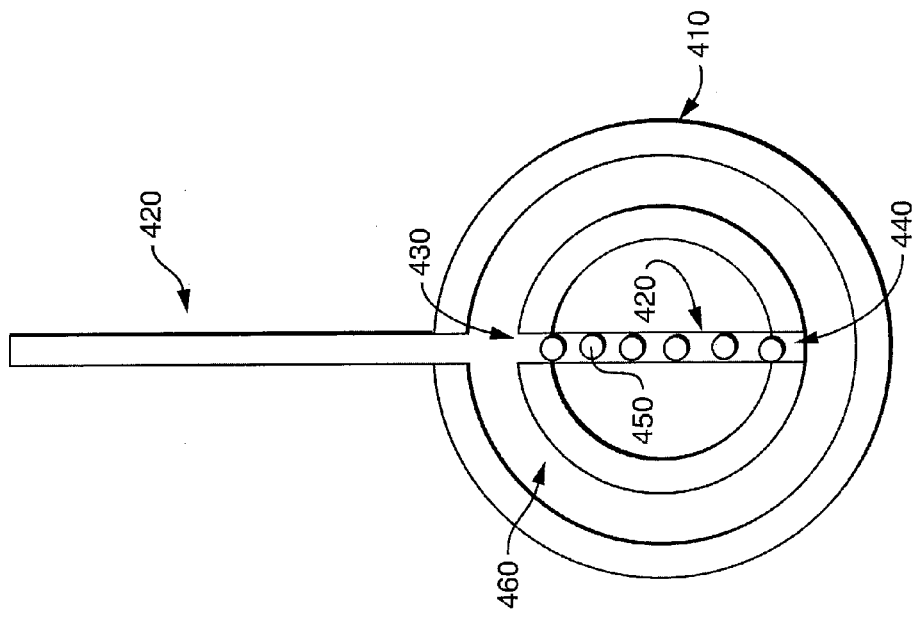
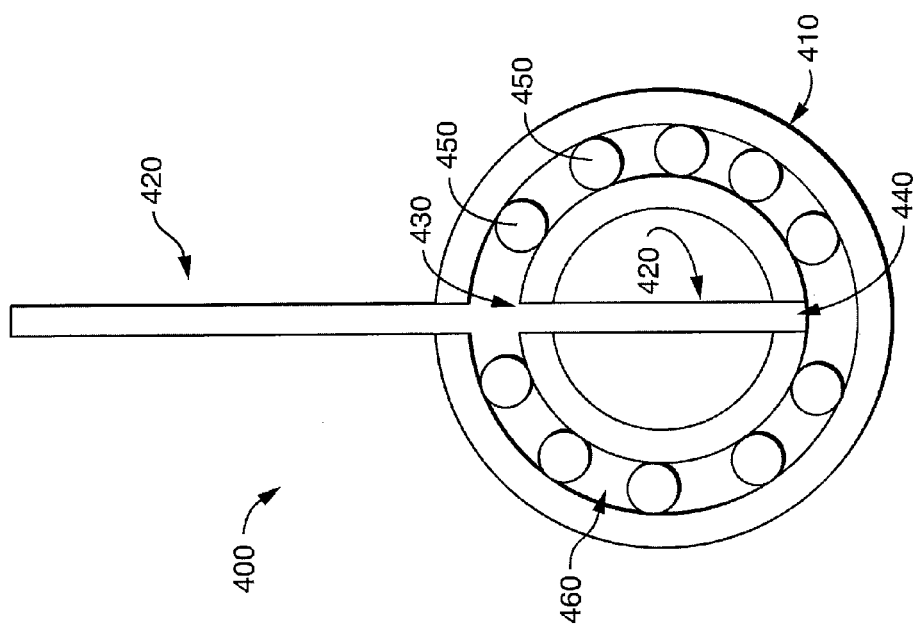

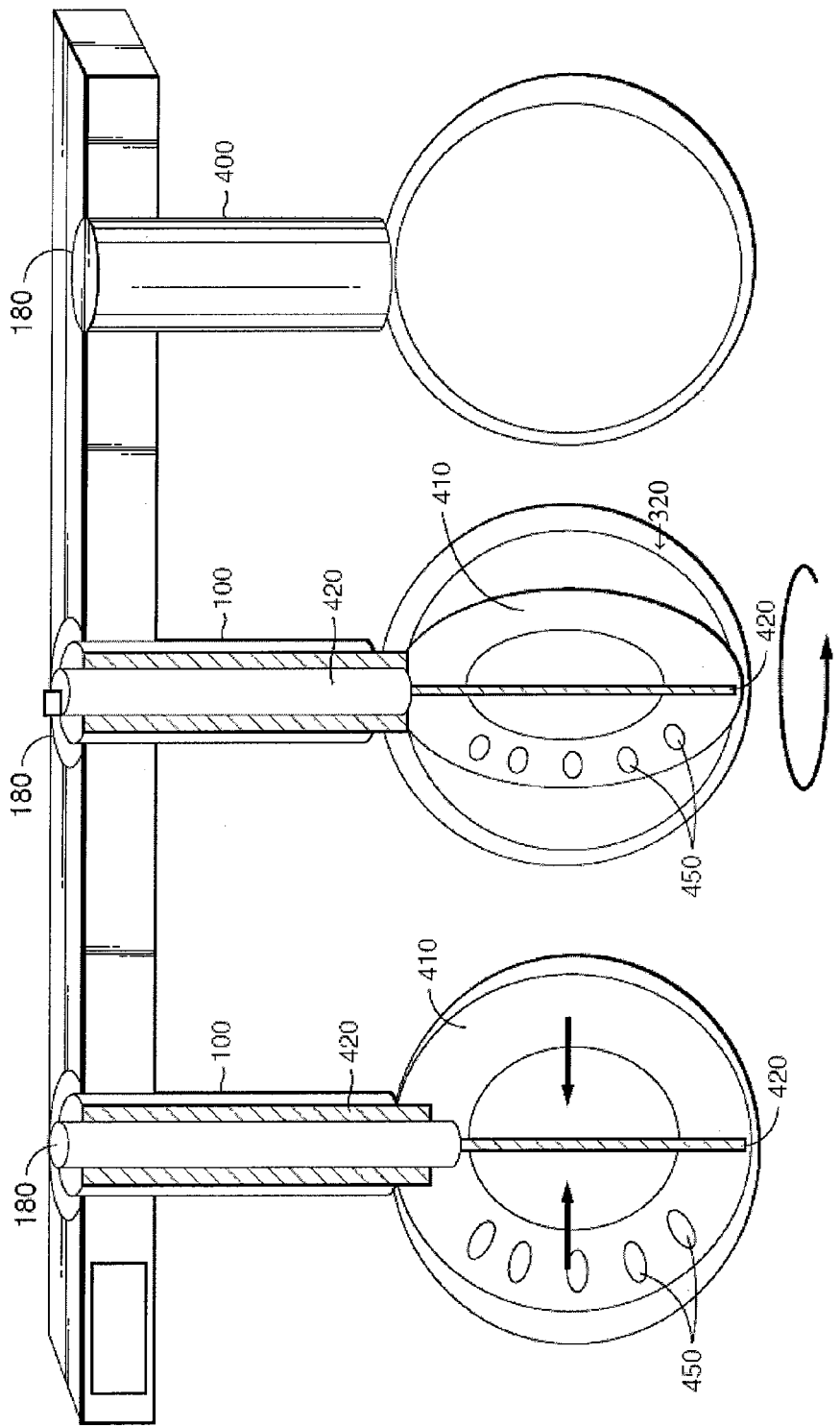

674

SURGICAL DEVICES AND RELATED METHODS THEREOF

CROSS-REFERENCE TO RELATED APPLICATIONS

The present application is a continuation-in-part of U.S. application Ser. No. 11/515,524 filed Sep. 5, 2006, now abandoned, which claims priority to U.S. Provisional Application 60/757,652, filed Jan. 10, 2006, and U.S. Provisional Application 60/713,639, filed Sep. 2, 2005, all of which are herein incorporated by reference.

FIELD OF THE INVENTION

The present invention relates to surgical devices and related methods of use. In particular, the present invention relates to surgical devices used, for example, for contacting and treating areas of the brain.

BACKGROUND

Brain tumors account for 85% to 90% of all primary central nervous system (CNS) tumors (see, e.g., Levin V. A., et al., Cancer: Principles and Practice of Oncology. 6th ed. Philadelphia, Pa.: Lippincott Williams & Wilkins, 2001, pp 2100-60; herein incorporated by reference in its entirety). Available registry data from the Surveillance, Epidemiology, and End Results (SEER) database for 1996 to 2000 indicate that the combined incidence of primary invasive CNS tumors in the United States is 6.6 per 100,000 persons per year, with an estimated mortality of 4.7 per 100,000 persons per year (see, e.g., Trends in SEER incidence and U.S. mortality using the joinpoint regression program 1975-2000 with up to three joinpoints by race and sex. In: Ries LAG, Eisner M P, Kosary CL, et al.: SEER Cancer Statistics Review, 1975-2000. Bethesda, Md.: National Cancer Institute, 2003; herein incorporated by reference in its entirety). Worldwide, approximately 176,000 new cases of brain and other CNS tumors were diagnosed in the year 2000, with an estimated mortality of 128,000 (see, e.g., Parkin D. M., et al., Int J Cancer 94 (2): 153-6, 2001; herein incorporated by reference in its entirety). In general, the incidence of primary brain tumors is higher in whites than in blacks, and mortality is higher in males than in females (see, e.g., Levin V. A., et al., Cancer: Principles and Practice of Oncology. 6th ed. Philadelphia, Pa.: Lippincott Williams & Wilkins, 2001, pp 2100-60; herein incorporated by reference in its entirety).

Metastatic tumors are among the most common mass lesions in the brain. In recent years the incidence of CNS metastasis has increased. This is because, for example, the median survival duration of cancer patients has increased as a result of modern therapies, increased availability of advance imaging techniques, and vigilant surveillance protocols. Unfortunately, some chemotherapeutic agents can weaken the blood-brain barrier (BBB) transiently and allow CNS seeding. Moreover, a number of commonly used chemotherapeutic agents do not cross the BBB, thus leaving the brain as a safe haven for tumor growth. Metastases from systemic cancer can affect brain parenchyma, its covering, and the skull. Different tumors metastasize to different organs preferentially. Generally, cells with similar origins are believed to have similar growth constraints and to embryologically express similar sets of adhesive molecules such as addressins. In the United States, incidence of metastatic brain tumor is exceeding that of primary brain tumor. Metastatic brain tumors comprise 50% of all brain tumors and as many as 30% of tumors diagnosed by imaging study alone. The incidence is estimated to be 100,000 new cases per year in the United States. In autopsy studies, over 20% patients with systemic neoplastic disease have brain metastasis.

The clinical presentation of various brain tumors is best appreciated by considering the relation of signs and symptoms to anatomy (see, e.g., Levin V. A., et al., Cancer: Principles and Practice of Oncology. 6th ed. Philadelphia, Pa.: Lippincott Williams & Wilkins, 2001, pp 2100-60; herein incorporated by reference in its entirety). General signs and symptoms include headache, gastrointestinal symptoms (e.g., nausea, loss of appetite, and vomiting) and changes in personality (e.g., changes in mood, mental capacity, and concentration). Whether primary, metastatic, malignant, or benign, brain tumors must be differentiated from other space-occupying lesions such as abscesses, arteriovenous malformations, and infarction, which can have a similar clinical presentation (see, e.g., Hutter A, et al., Neuroimaging Clin N Am 13 (2): 237-50, x-xi, 2003; herein incorporated by reference in its entirety).

Surgery is the treatment of choice for accessible brain tumors. Accessible tumors are those that can be surgically removed without causing severe neurological damage. Deeply seated tumors (e.g., brain tumors located in the brain stem, the thalamus, the motor area, and the deep areas of gray matter) may be inaccessible, and as such, inoperable. The goal of surgery is to remove all or most of the visible tumor. Many benign tumors are treated only by surgery. Most malignant tumors require additional treatment. Malignant tumors lack distinct borders. They often invade nearby normal brain tissue. Tumor cells may also spread throughout the brain and spine by way of the cerebrospinal fluid. But, even partial tumor removal is beneficial.

There are several purposes of brain tumor related neurosurgery. One purpose of brain tumor related surgery is to remove as much tumor as possible. Partial brain tumor removal (e.g., debulking) provides relief of symptoms, improved quality of life, and a smaller tumor burden for other treatment modalities. Brain tumor related neurosurgery also assists in establishing an exact diagnosis. For example, removal of a sample of tumor (e.g., a tumor biopsy) to be examined under a microscope in the laboratory provides an exact diagnosis. Furthermore, brain tumor related neurosurgery provides access for other treatments. For example, during neurosurgery radiation implants or chemotherapy-impregnated wafers may be delivered to the brain tumor. Biopsy alone is performed when the tumor is inoperable or when surgery must be delayed. Resection (e.g., surgical removal of a tumor) is the treatment of choice whenever possible.

Neurosurgery, however, demands special considerations. Obtaining surgical access to brain tumors requires the creation of an opening in the skull (called a craniotomy). Most often, a craniotomy involves a large incision and dissection of other soft tissue that results in significant postoperative pain and discomfort. Furthermore, reaching deep tumors in the brain requires openings into the surface of the brain itself. This brain dissection and manipulation can result in neurological deficits.

What is needed are improved neurosurgical techniques for accessing brain locations. Additionally, what are needed are improved devices assisting in neurosurgical techniques that limit soft tissue dissection and potential brain manipulation and damage. Additionally, what is needed are improved devices for cutting, cauterizing and aspirating brain tumors through small openings in the skull and brain tissue.

SUMMARY OF THE INVENTION

The present invention relates to surgical devices and related methods of use. In particular, the present invention relates to surgical devices used, for example, for contacting and treating areas of the brain, including deeply seated areas. Generally, deeply seated tumors are considered inoperable. The present invention, however, provides devices capable of accessing deeply seated areas of the brain (e.g., brain tumors, hematomas, infections) while minimizing the risk of brain damage.

In some embodiments, the present invention provides probe devices comprising: a) a tubular central stem, wherein the tubular central stem comprises a proximal portion, a distal portion, and a distal end, wherein a plurality of suction and cutting openings are formed in the distal portion of the tubular central stem, wherein the tubular central stem is configured to allow cutting of tissue with the plurality of cutting openings, and allow aspiration of the tissue through the plurality of suction openings; b) a probe sleeve, wherein the probe sleeve comprises a proximal portion, and a distal portion, wherein the proximal portion encloses most or all of the proximal portion of the tubular central stem; c) at least one wire loop, wherein the at least one wire loop is operably attached to the distal end of the tubular central stem and extends beyond the distal portion of the probe sleeve, and wherein the at least one wire loop is: i) configured for cutting tissue, ii) configured for rotating around the distal portion of the tubular central stem, and iii) configured to outwardly expand and contract; and d) a loop expander and rotation motor mechanism which is operably linked to the at least one wire loop and configured to cause rotation and outward expansion of the at least one wire loop, wherein the loop expander and rotation mechanism is located in the probe sleeve.

In certain embodiments, the present invention provides systems comprising: a) a probe device comprising: i) a tubular central stem, wherein the tubular central stem comprises a proximal portion, a distal portion, and a distal end, wherein a plurality of suction and cutting openings are formed in the distal portion of the tubular central stem, wherein the tubular central stem is configured to allow cutting of tissue with the plurality of cutting openings, and allow aspiration of the tissue through the plurality of suction openings; ii) a probe sleeve, wherein the probe sleeve comprises a proximal portion, and a distal portion, wherein the proximal portion encloses most or all of the proximal portion of the tubular central stem; iii) at least one wire loop, wherein the at least one wire loop is operably attached to the distal end of the tubular central stem and extends beyond the distal portion of the probe sleeve, and wherein the at least one wire loop is: A) configured for cutting tissue, B) configured for rotating around the distal portion of the tubular central stem, and C) configured to outwardly expand and contract; and iv) a loop expander and rotation motor mechanism which is operably linked to the at least one wire loop and configured to cause rotation and outward expansion of the at least one wire loop, wherein the loop expander and rotation mechanism is located in the probe sleeve; and b) at least one additional component selected from the group consisting of: i) an energy generating component, ii) an irrigation supply component; iii) a system controller component; iv) a cannula, wherein the probe is configured to fit through the cannula; and v) a mounting mechanism.

In certain embodiments, the energy generating component comprises an RF generating component. In other embodiments, the probe is inserted through the cannula (e.g., where the depth of insertion determines the size of the expanded wire loops).

In certain embodiments, the at least one wire loop has a proximal portion and a distal portion, and wherein downward thrust on the proximal portion of the at least one wire by the loop expander and rotation motor mechanism causes outward expansion of the at least one wire loop. In other embodiments, the probes further comprise an energy generator connection (RF connection), wherein the energy generator connection is attached to the probe sleeve. In some embodiments, the probes further comprise an irrigation fluid input port, wherein the irrigation fluid input port is attached to the probe sleeve. In particular embodiments, the probes further comprise a vacuum port connection, wherein the vacuum port connection is attached to the probe sleeve. In other embodiments, the probes further comprise a cutting motor mechanism, wherein the cutting motor mechanism is attached to the tubular central stem. In additional embodiments, the probes further comprise a loop swivel attachment, wherein the at least one wire loop is operably attached to the distal end of the tubular central stem via the loop swivel attachment.

In some embodiments, the at least one wire loop expands out in a half-circle or egg-beater shape. In additional embodiments, the at least one wire loop comprises two, three, four, five, six, seven, eight, nine, or ten wire loops.

In certain embodiments, the present invention provides a device comprising a cannula member. In preferred embodiments, the cannula member comprises a tubular extension comprising proximal and distal ends, the tubular extension having a longitudinal axis and having therein a hollow channel parallel to the longitudinal axis, the hollow channel running the length of the tubular extension through the proximal and distal ends, wherein upon insertion into a bone hole said tubular extension extends beyond said bone hole and into the body cavity surrounding said bone hole; and an attachment member on the proximal end, the attachment member configured such that as the tubular extension is inserted into a bone hole the attachment member engages the outside of the bone hole thereby securing the device within the bone hole. The cannula member is configured to be inserted into a bone hole at any desired angle (e.g., 90 degrees, 80 degrees, 45 degrees, 20 degrees).

In some embodiments, the attachment member comprises an overhang portion that extends beyond the tubular extension, wherein the overhang portion is configured to engage the surface of a bone thereby securing the cannula device within a bun hole. In other embodiments, the overhang portion has therein a plurality of holes configured to receive fastening agents. In some embodiments, the attachment member configured such that as the cannula device is inserted into a bone hole such that the attachment member engages the outside of the bone hole thereby securing the device within the bone hole. The overhang portion may be secured to the surface of a bone hone hole in any manner (e.g., adhesive glue, threaded fasteners).

In preferred embodiments, the cannula member has therein a removable stylet. The cannula member is not limited to a particular type, size, or shape of stylet. In preferred embodiments, the stylet assists in navigating the cannula member through the brain. In preferred embodiments, the stylet is removed after positioning of the cannula member within the brain.

In preferred embodiments, the bone hole passes through the bone. In other preferred embodiments, the material of the cannula device comprises polyacetal although any suitable material may be used (e.g., metals, ceramics, plastics, etc.). In some embodiments, the bone is the cranial bone and the bone hole is a bun hole.

In preferred embodiments, the cannula member further comprises or is associated with an endoscopic camera or imaging component or navigation system that permits or assists in placement, positioning, and/or monitoring of the device.

The tubular extension is not limited to a particular length. In preferred embodiments, the length of the tubular extension is at least 2 cm, at least 5 cm in length, and at least 10 cm in length. In other embodiments, the length of the tubular extension is between 1-5 cm, while in other embodiments, the length of the tubular extension is between 0.1 cm and 10 cm. In preferred embodiments, the length of the tubular extension may be varied so that it can reach lesions (e.g., tumors, vascular malformations, infections, blood clots) of different depths. The tubular extension is not limited to a particular diameter measurement. In preferred embodiments, the diameter of the tubular extension is at least 5 mm in diameter, at least 10 mm in diameter, and at least 20 mm in diameter. In some embodiments, the diameter of the tubular extension is between 1-2 cm, while in other embodiments, the diameter of the tubular extension is between 0.1 cm and 5 cm. In particularly preferred embodiments, the length and diameter measurements of the tubular extension are such that additional medical instruments (e.g., ablative devices, biopsy devices, navigation devices, aspiration devices, imaging devices, ultrasound probes, etc.) may be positioned within the tubular extension. The diameter of the tubular extension is preferably kept as small as possible to minimize the amount of bone that is removed and to minimize the exposure to the environment.

In some embodiments the cannula member may comprise more than one tubular extension allowing for simultaneous passage of additional medical instruments (e.g. ultrasound probes, ablative devices, biopsy devices, navigation devices, aspiration devices, imaging devices, etc.).

In preferred embodiments, the attachment member comprises a protruding lip surrounding the edge of the proximal end. The protruding lip is not limited to a particular size. In preferred embodiments, the protruding lip extends outward from the tubular extension a distance between, for example, 0.1 cm and 2 cm. In other preferred embodiments, the protruding lip contains at least one attachment hole, wherein the at least one attachment hole is configured to accept a fastening agent such that upon insertion of the fastening agent into the attachment hole the device is secured within the bone hole. In still other preferred embodiments, the fastening agent is a threaded fastener.

In some embodiments the cannula member may pivot in relationship to the proximal protruding lip so that the cannula can be inserted at different angles into the bone hole or the underlying tissue surface. In certain embodiments, a fastening agent at the proximal end can secure the cannula in position in relation to the protruding lip.

In some embodiments the cannula member may slide through the proximal protruding lip so that length of penetration of the cannula into the tissue or the bone hole can be modified.

In some embodiments, the protruding lip has protruding lip fixtures (e.g., edges, lips, tongues, etc.) allowing additional medical instruments (e.g., ablative devices, biopsy devices, navigation devices, aspiration devices, imaging devices, etc.) to lock onto the tubular extension and prevent undesired movement of the medical instrument.

In certain embodiments, the present invention provides a device comprising a cutting and cauterizing member. In preferred embodiments, the cutting and cauterizing member comprises a motor operably connected to the wire or wires, the wire or wires configured for extension and retraction from the motor, the motor configured to continuously rotate the wire or wires such that a contacting of the continuously rotating wire or wires with the tissue results in a cutting of the tissue; and an energy source operably connected to the wire or wires, the energy source configured to deliver energy (e.g., laser energy, radio-frequency energy, electrical energy) to the wire or wires such that the energy is emitted from the at least one wire, wherein a contacting of the at least one wire emitting energy with the tissue results in a cauterizing of the tissue.

In preferred embodiments, the energy is electrical energy. In preferred embodiments, any number of wires may be used (e.g., 2, 3, 5, 7, 10 . . . 15). In other preferred embodiments, the wire is configured to assume any desired shape (e.g., circular, elliptical, oval, substantially circular, coiled). The wire is not limited to a particular length depending on the depth and size of the lesion (e.g., tumor, vascular malformation, infection, blood clot, etc.). In preferred embodiments, the length of the wire is at least 0.25 cm in length (e.g., 0.5 cm in length, 0.75 cm in length, 1 cm in length, 2 cm in length . . . 20 cm in length). The wire is not limited to a particular diameter measurement. In preferred embodiments, the diameter of the wire is at least 0.05 mm (e.g., 0.075 mm, 0.01 mm . . . 0.05 mm, etc.).

In preferred embodiments, the device is configured for insertion through the cannula devices of the present invention. In preferred embodiments, the device is configured to lock into the cannula device so as to prevent it from undesired movement.

In certain embodiments, the present invention provides a device comprising a member for aspirating a tissue. In preferred embodiments, the member for aspirating a tissue comprises at least one suction arm comprising an opening end and a closed end, and the suction arm having therein a hollow channel running the length of the suction arm through the open end. In preferred embodiments, the suction arm has therein at least one suction opening. In preferred embodiments, the suction arm is configured for expansion or retraction into a desired shape. In preferred embodiments, the suction member is attached to the at least one suction arm, the suction member configured to generate a suction force through the at least one suction arm, the suction member configured to continuously rotate the at least one suction arm, wherein a contacting of the continuously rotating at least one suction arm with the tissue results in aspiration of at least a portion of the tissue through the at least one suction opening. In other preferred embodiments, the suction member has therein at least one suction opening.

In preferred embodiments, the at least one suction arm comprises at least two suction arms (e.g., 2, 3, 5, 7, 10 . . . 15 suction arms). The suction arm is not limited to a particular length. In preferred embodiments, the length of the at least one suction arm is at least 1 cm (e.g., at least 1.5 cm, at least 2 cm . . . at least 5 cm). In preferred embodiments, the dimensions of the suction arm are configured such that the suction arm is capable of expanding into the shape of a circle with at least 1 cm diameter. In preferred embodiments, the diameter of the at least one suction arm is at least 0.5 cm (e.g., 1 cm, 2 cm . . . 5 cm). In other preferred embodiments, the aspirated tissue is collected in the suction member.

In preferred embodiments, the tissue is a tumor (e.g., a brain tumor), a hematoma, abscess, or contused brain tissue. In preferred embodiments, the at least one suction opening comprises at least 2 suction openings (e.g., 2, 3, 5, 10, 20, 50 . . . 100 suction arms). In preferred embodiments, the device is configured for insertion through the cannula devices of the present invention.

In certain embodiments, the present invention provides a device comprising a hemostasis promoting member. In preferred embodiments, the hemostasis promoting member comprises a hemostasis member, the hemostasis member configured for inflation and deflation; and an expansion member attached to the hemostasis member, the expansion member configured to inflate the hemostasis member, wherein upon a contacting of the inflated hemostasis member with the tissue promotes hemostasis of the tissue.

In preferred embodiments, the hemostasis member is a balloon. In preferred embodiments, the balloon is not limited to a particular type of material (e.g., rubber, plastic, nylon, or mixture thereof). In preferred embodiments, the exterior of the balloon is coated with a pharmaceutical agent (e.g., thrombogenic agent, wound healing agent, anti-cancer agent). In preferred embodiments, the diameter of an inflated balloon at least 0.5 cm (e.g., 1 cm, 2 cm . . . 5 cm). In preferred embodiments, the length of an inflated balloon is at least 0.5 cm (e.g., 1 cm, 2 cm . . . 5 cm). In preferred embodiments, the tissue is a hemorrhaging tissue. In other preferred embodiments, the hemostasis member conforms in shape to a body cavity. In still other preferred embodiments, the expansion member is configured to deflate the hemostasis member. In preferred embodiments, the device is configured for insertion through the cannula devices of the present invention. In preferred embodiments, the hemostasis member is able to induce hemostasis within a hemorrhaging body cavity (e.g., a hemorrhaging brain tumor cavity). In preferred embodiments, the tip of an inflated balloon may have an opening to allow, for example, injection of solutions or other materials into the cavity. In preferred embodiments, the tip of an inflated balloon may have an opening to allow for aspiration of solutions or other materials from the cavity.

In certain embodiments, the present invention provides a device comprising a cutting and cauterizing member, an aspiration member, and a hemostasis promoting member. In certain embodiments, the present invention provides a device comprising a cutting and cauterizing member, and an aspiration member. In certain embodiments, the present invention provides an aspiration member, and a hemostasis promoting member. In certain embodiments, the present invention provides a cutting and cauterizing member, and a hemostasis promoting member.

In certain embodiments, the present invention provides a system comprising an accessory agent positioned within a cannula member. In preferred embodiments, the accessory agent is selected from the group consisting of a cutting and cauterizing member, an aspiration member, and a hemostasis member.

In certain embodiments, the present invention provides a kit or system comprising at least two accessory agents selected from the group consisting of a device comprising a cannula member, a device comprising a cutting and cauterizing member, a device comprising an aspiration member, and a device comprising a hemostasis member. In preferred embodiments, the kit or system further comprises at least of an additional accessory agent selected from the group consisting of an ablation device, an imaging device, and a pharmaceutical agent. In preferred embodiments, the kit or system comprises a device comprising a cannula member, and a device comprising a cutting and cauterizing member. In preferred embodiments, the kit or system comprises a device comprising a cannula member, and a device comprising an aspiration member. In preferred embodiments, the kit or system comprises a device comprising a cannula member, and a device comprising a hemostasis member. In preferred embodiments, the kit or system comprises a device comprising a cannula member, and a device comprising a cutting and cauterizing member and an aspiration member. In preferred embodiments, the kit or system comprises a device comprising a cannula member, and a device comprising an aspiration member and a hemostasis member. In preferred embodiments, the kit or system comprises a device comprising a cannula member, and a device comprising a cutting and cauterizing member and a hemostasis member. In preferred embodiments, the kit or system comprises a device comprising a cannula member, a device comprising a cutting and cauterizing member and an aspiration member, and a device comprising a hemostasis member. In preferred embodiments, the kit or system comprises a device comprising a cannula member, a device comprising an aspiration member and a hemostasis member, and a device comprising a cutting and cauterizing member. In preferred embodiments, the kit or system comprises a device comprising a cannula member, a device comprising a cutting and cauterizing member and a hemostasis member, and a device comprising an aspiration member. In preferred embodiments, the kit or system comprises a device comprising a cannula member, and a device comprising a cutting and cauterizing member, an aspiration member, and a hemostasis member. In preferred embodiments, the kit or system comprises a device comprising a cannula member, a device comprising a cutting and cauterizing member, a device comprising an aspiration member, and a device comprising a hemostasis member. In preferred embodiments, the kit or system comprises a device comprising a cannula member, a device comprising a cutting and cauterizing member, and a device comprising an aspiration member. In preferred embodiments, the kit or system comprises a device comprising a cannula member, a device comprising a cutting and cauterizing member, and a device comprising a hemostasis member. In preferred embodiments, the kit or system comprises a device comprising a cannula member, a device comprising an aspiration member, and a device comprising a hemostasis member. In preferred embodiments, the kit or system comprises a device comprising a cutting and cauterizing member and an aspiration member. In preferred embodiments, the kit or system comprises a device comprising an aspiration member and a hemostasis member. In preferred embodiments, the kit or system comprises a device comprising a cutting and cauterizing member and a hemostasis member. In preferred embodiments, the kit or system comprises a device comprising a cutting and cauterizing member and an aspiration member, and a device comprising a hemostasis member. In preferred embodiments, the kit or system comprises a device comprising an aspiration member and a hemostasis member, and a device comprising a cutting and cauterizing member. In preferred embodiments, the kit or system comprises a device comprising a cutting and cauterizing member and a hemostasis member, and a device comprising an aspiration member. In preferred embodiments, the kit or system comprises a device comprising a cutting and cauterizing member, an aspiration member, and a hemostasis member. In preferred embodiments, the kit or system comprises a device comprising a cutting and cauterizing member, a device comprising an aspiration member, and a device comprising a hemostasis member. In preferred embodiments, the kit or system comprises a device comprising a cutting and cauterizing member, and a device comprising an aspiration member. In preferred embodiments, the kit or system comprises a device comprising a cutting and cauterizing member, and a device comprising a hemostasis member. In preferred embodiments, the kit or system comprises a device comprising an aspiration member, and a device comprising a hemostasis member.

In certain embodiments, the present invention provides a method of treating a brain tissue mass, comprising a) providing i) a subject with a brain tissue mass; ii) a cannula device secured within a bun hole such that the cannula device is contacting the brain tissue mass, the cannula device comprising a tubular extension comprising an proximal and distal ends, the tubular extension having a longitudinal axis and having therein a hollow channel parallel to the longitudinal axis, the hollow channel running the length of the tubular extension through the proximal and distal ends, wherein upon insertion into a bone hole the tubular extension extends beyond the bone hole and into the body cavity surrounding the bone hole; and an attachment member on the proximal end of the tubular extension, wherein the attachment member comprises an overhang portion that extends beyond the tubular extension, wherein the overhang portion engages the surface of said bone thereby securing said cannula device within said burr hole; and iii) an accessory agent; and b) positioning the accessory agent within the tubular extension of the cannula device such that the accessory agent is contacting the brain tissue mass; and c) treating the brain tissue mass with the accessory agent. In preferred embodiments, the brain tissue mass is a brain tumor. In preferred embodiments, the brain tumor is a deeply seated brain tumor. In preferred embodiments, the attachment member is configured such that as the tubular extension is inserted into the bone hole the attachment member engages the outside of the bone hole thereby securing the device within the bone hole.

In preferred embodiments, the overhang portion has therein a plurality of holes configured to receive fastening agents. In some embodiments, the holes within the overhang portion have therein threaded fasteners such that the threaded fasteners engage the surface of the bun hole.

In some embodiments, the attachment member configured such that as the tubular extension is inserted into the burr hole the attachment member engages the outside of the bone hole thereby securing the device within the bone hole.

In preferred embodiments, the accessory agent is selected from the group consisting of an ablation device, an imaging device, a pharmaceutical agent, a device comprising a cutting and cauterizing member, a device comprising an aspiration member, and a device comprising a hemostasis promoting member, a device comprising a cutting and cauterizing member and an aspiration member, a device comprising an aspiration member and a hemostasis member, a device comprising a cutting and cauterizing member and a hemostasis member, and a device comprising a cutting and cauterizing member, an aspiration member, and a hemostasis promoting member.

In certain embodiments, the present invention provides a method of treating a brain tissue mass, comprising a) providing i) a subject with a brain tissue mass; ii) a surgical device selected from the group consisting of a device comprising a cutting and cauterizing member, a device comprising an aspiration member, a device comprising a hemostasis promoting member, a device comprising a cutting and cauterizing member and an aspiration member, a device comprising an aspiration member and a hemostasis member, a device comprising a cutting and cauterizing member and a hemo stasis member, and a device comprising a cutting and cauterizing member, an aspiration member, and a hemostasis promoting member; b) contacting the brain tissue mass with the surgical device; and c) treating the brain tissue mass with the surgical device.

In certain embodiments, the present invention provides a method of treating a brain tissue mass, comprising a) providing a subject with a brain tissue mass; a device secured within a bun hole of the subject's cranium such that the device is contacting the brain tissue mass, the device comprising a cannula member; and a surgical device; and b) positioning the surgical device through the cannula member such that the surgical device is contacting the brain tissue mass; and c) treating the brain tissue mass with the surgical device.

In preferred embodiments, the cannula member comprises a tubular extension comprising proximal and distal ends, the tubular extension having a longitudinal axis and having therein a hollow channel parallel to the longitudinal axis, the hollow channel running the length of the tubular extension through the proximal and distal ends. In preferred embodiments, the cannula member comprises an attachment member attached to the proximal end of the tubular extension, the attachment member configured such that as the cannula device is inserted into a bone hole the attachment member engages the surface of the bone thereby securing the cannula device within the burr hole.

In preferred embodiments, the brain tissue mass is a brain tumor. In preferred embodiments, the surgical device is selected from the group consisting of a device comprising a cutting and cauterizing member, a device comprising an aspiration member, and a device comprising a hemostasis promoting member. In some embodiments, the surgical device is the device comprising a cutting and cauterizing member, and the treating step comprises cutting and cauterizing the brain tissue mass with the device comprising a cutting and cauterizing member. In preferred embodiments, the surgical device is the device comprising an aspiration member, and the treating step comprises suctioning at least a portion of the brain tissue mass with the aspiration member. In preferred embodiments, the surgical device is the device comprising a hemostasis promoting member, and the treating step comprises inducing hemostasis on at least a portion of the subject's brain tissue with the device comprising a hemostasis promoting member.

In certain embodiments, the present invention provides a kit comprising a) a device comprising a cannula member, the cannula member comprising a tubular extension comprising proximal and distal ends, the tubular extension having a longitudinal axis and having therein a hollow channel parallel to the longitudinal axis, the hollow channel running the length of the tubular extension through the proximal and distal ends, the tubular extension configured such that upon insertion into a bone the tubular extension extends into the body cavity surrounding the bone hole; and an attachment member attached to the proximal end of the tubular extension, the attachment member configured such that as the cannula device is inserted into a bone hole the attachment member engages the surface of the bone thereby securing the cannula device within the bone hole; and b) at least one surgical device selected from the group consisting of a device comprising a cutting and cauterizing member, a device comprising an aspiration member, and a device comprising a hemostasis promoting member.

In preferred embodiments, the at least one surgical device is at least 2 or more of the surgical devices. In preferred embodiments, the at least one surgical device is at least 3 or more of the surgical devices. In preferred embodiments, the hemostasis promoting member comprises a thrombogenic agent.

BRIEF DESCRIPTION OF THE DRAWINGS

FIGS. 5A-B show side views of a cutting and cauterizing device positioned within a cannula device secured within a bun hole.

FIGS. 6A-C show exemplary shapes the cutting and cauterizing wire may assume.

FIGS. 7A-B show side views of an aspiration device embodiment of the present invention.

FIGS. 9A-C show an aspiration device positioned within a cannula device secured within a bun hole.

FIG. 18A shows one embodiment of a probe device with 4 loops in the unexpanded position (straight arrows), while

DEFINITIONS

Figure 1:
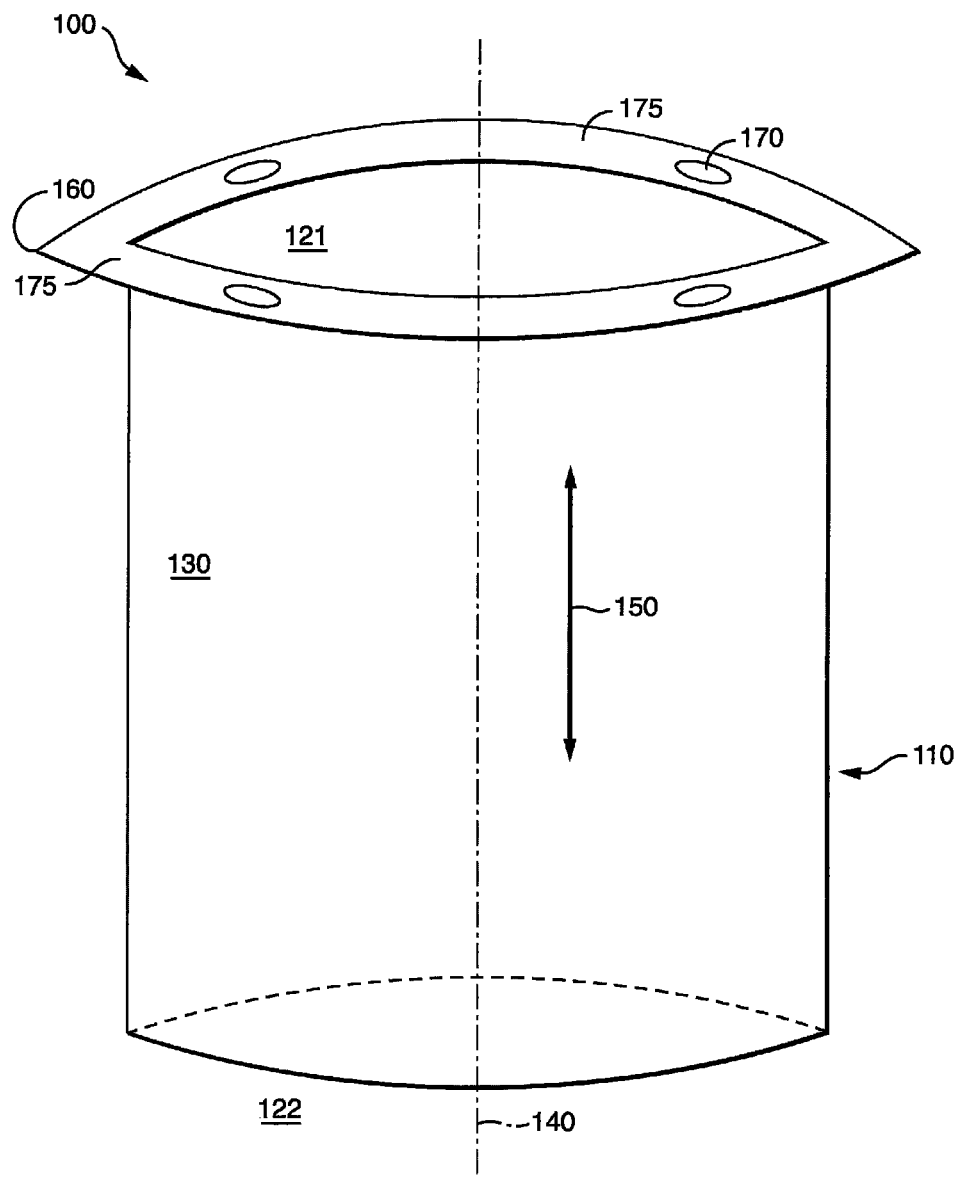
FIG. 1 shows a side view of a cannula device embodiment of the present invention.

To facilitate an understanding of the invention, a number of terms are defined below.

As used herein, the term "bone hole" refers to a surgically inserted hole through a bone (e.g., cranium, mandible, cervical vertebrae, clavicle, scapula, sternum, ribs, humerus, thoracic vertebrae, lumbar vertebrae, ulna, radius, pelvis, carpals, phalanges, sacrum, metacarpals, femur, patella, tibia, fibula, tarsals, metatarsals).

As used herein, the term "bun hole" refers to a surgically inserted hole through the cranium. Generally, a "burr hole" is utilized during neurosurgical procedures.

As used herein, the term "subject" refers to any living entity. Examples of subject include, but are not limited to, cats, dogs, mice, primates, humans, birds, and fish.

As used herein, the term "tissue" refers to a part of a group of cells within a subject's body. An example of a tissue is a brain tumor.

As used herein, the term "tumor" refers to an abnormal mass of tissue that results from, for example, excessive cell division. A tumor may also represent other mass-occupying lesions such as hematomas, blood clots, or infections.

As used herein, the term "brain tumor" refers to a tumor located within a subject's brain. Examples of brain tumors include, but are not limited to, astrocytoma tumors, glioma tumors, atypical teratoid/rhabdoid tumors, brain stem gliomas, choroid plexus tumors, craniopharyngiomas, ependymoma tumors, ganglioglioma tumors, germ cell tumors, gliomatosis cerbri tumors, infant brain tumors, medulloblastoma tumors, oligodendroglioma tumors, and optic pathway tumors. Brain tumors can be located near a subject's cranium surface (e.g., within 2 cm of the subject's cranium surface) or located in a deeply seated region of the brain (e.g., at least 2 cm away from the subject's cranium surface).

As used herein, the term "deeply seated brain tumor" refers to brain tumors located in difficult to reach areas of the brain (e.g., located at least 2 cm away from the subject's cranium surface). Examples of deeply seated brain tumors include, but are not limited to, brain tumors located in the brain stem, brain tumors located in the thalamus, brain tumors located in the motor area, and brain tumors located in the deep areas of gray matter.

As used herein, the term "resection" refers to excision of a portion or all of a tissue structure.

As used herein, the term "biopsy" refers to a procedure that involves obtaining a tissue specimen to establish a precise diagnosis. Biopsies can be accomplished, for example, with a biopsy needle or by an open surgical incision.

As used herein, the term "brain cancer" refers to forms to cancer located within a subject's brain. Examples of brain cancer include, but are not limited to, childhood brain stem glioma, childhood cerebellar astrocytoma, childhood cerebral astrocytoma/malignant glioma, childhood ependymoma, childhood medulloblastoma, childhood supratentorial primitive neuroectodermal tumors and pineoblastoma, and visual pathway and hypothalamic glioma.

As used herein, the term "inflexible" in reference to a tubule extension, refers to a tubule extension that is rigid such that it is resistant to bending about its longitudinal axis. A tubule extension is considered inflexible if it cannot be bent about its longitudinal axis unless such force is applied that causes a permanent bend in the tubule extension.

DETAILED DESCRIPTION

The present invention relates to surgical devices and related methods of use. In particular, the present invention relates to surgical devices used for contacting and treating brain tissue (e.g., brain tumors). FIGS. 1-11 illustrate various preferred embodiments of the surgical devices and related methods thereof. The present invention is not limited to these particular embodiments.

The illustrated and preferred embodiments describe the devices of the present invention in terms of neurosurgical applications (e.g., brain tumor resection, brain tumor biopsy, brain tumor imaging, brain hematoma evacuation, decompression of contused or damage brain). However, it should be appreciated that the devices are not limited to neurosurgical applications. Indeed, the devices of the present invention have application in any procedure requiring access to a body cavity through a bone structure (e.g., spinal surgery, bone marrow applications, liver tumor surgery, etc.).

Cannula Device

FIG. 1 shows a side view of a cannula device 100 embodiment of the present invention. The cannula device 100 is not limited to a particular material composition (e.g., synthetic rubber, titanium, biocompatible plastic, polyacetal, elastomeric material, polyurethane, polyethylene, stainless steel, metal, or mixture thereof). In preferred embodiments, the material composition of the cannula device 100 comprises polyacetal. In preferred embodiments, the cannula device 100 is configured to engage and attach within a bone hole (e.g., a burr hole) (described in more detail below). In preferred embodiments, the cannula device 100 is configured to provide a passage from the outside of a bone hole to an interior body cavity (e.g., a deeply seated brain tumor) (described in more detail below).

Still referring to FIG. 1, in some embodiments, the cannula device 100 generally comprises a tubular extension 110 with a tubular extension proximal end 121 a tubular extension distal end 122, a tubular extension exterior surface 130, and a tubular extension longitudinal axis 140. In preferred embodiments, the tubular extension 110 has therein a tubular extension hollow channel 150 running the length of the tubular extension 110 through the two tubular extension proximal and distal ends 121 and 122. The tubular extension 110 is not limited to a particular shape (e.g., spherical, oval, conical). In preferred embodiments, the shape of the tubular extension 110 is cylindrical. In some preferred embodiments, the tubular extension 110 has an endoscopic camera positioned on the tubular extension distal end 122 (see, e.g., Pediatric Endoscope System, Richard Wolf Neuroendoscopy; herein incorporated by reference in its entirety). In some preferred embodiments, the tubular extension 110 has a navigation system (see, e.g., Medtronic Neurosurgery navigation products including, but not limited to, StealthStation TREON plus Medtronic Navigational System, StealthStation TRIA plus Medtronic Navigational System, and StealthStation AXIEM Electromagnetic Medtronic Navigational System) positioned on the tubular extension proximal end 121 facilitating accurate insertion of the cannula device 100 into a body cavity.

Still referring, in preferred embodiments, the tubular extension 110 has therein a removable stylet. The cannula member is not limited to a particular type, size, or shape of stylet. In preferred embodiments, the stylet assists in navigating the cannula device 100 through the brain. In preferred embodiments, the stylet is a rigid metal shaft with drill or screw type structures and a robust (e.g., hardened) end (e.g., pointed end, curved end). Other suitable stylet configurations are described in, for example, U.S. Pat. No. 6,033,411 and U.S. Patent Application Publication No. 2002-0188300, each of which is herein incorporated by reference in their entireties. In preferred embodiments, the stylet is removed after positioning of the cannula device 100 within the brain.

Still referring to FIG. 1, the tubular extension 110 is not limited to a particular length. In preferred embodiments, the length of the tubular extension 110 is at least 2 cm, at least 5 cm in length, and at least 10 cm in length. In preferred embodiments, the length of the tubular extension 110 may be varied so that it can reach lesions (e.g., tumors, vascular malformations, infections, blood clots) of different depths. The tubular extension 110 is not limited to a particular diameter measurement. In preferred embodiments, the diameter of the tubular extension 110 is at least 5 mm in diameter, at least 10 mm in diameter, and at least 20 mm in diameter. In preferred embodiments, the canula devices 100 (e.g., designed for neurosurgical procedures) may range in size from, for example, 0.1 to 10 cm in length and 0.1 to 5 cm in diameter. In certain embodiments, the size dimensions for canula devices 100 (e.g., designed for neurosurgical applications) ranges from 1 to 5 cm in length and 1 to 2 cm in diameter. In particularly preferred embodiments, the length and diameter measurements of the tubular extension 110 are such that additional medical instruments (e.g., ablative devices, biopsy devices, navigation devices, aspiration devices, imaging devices, etc.) may be positioned within the tubular extension 110. The diameter of the tubular extension 110 is preferably kept as small as possible to minimize the amount of bone that is removed and to minimize the exposure to the environment. In certain embodiments, the cannula device 100 may comprise of two or more hollow channels 150 such that different medical devices can be simultaneously be positioned within the tubular extension 110.

Still referring to FIG. 1, in preferred embodiments, as a cannula device 100 is positioned within a bone hole (e.g., burr hole), the tubular extension 110 fits within the bone hole such that the tubular extension exterior surface 130 engages both the interior sides of the bone hole and the interior body cavity situated beyond the bone hole (e.g., the brain) (described in more detail below). In preferred embodiments, the tubular extension 110 is flexible such that upon insertion into a body cavity (e.g., brain), the tubular extension may assume a shape consistent with the body cavity. In other embodiments, the tubular extension 110 is inflexible. In preferred embodiments, the cannula device 100 may be inserted at any angle with respect to the bone hole (e.g., 90, 80, 70, 60, 50, 40, 30, 20, 10, 1 degree angle).

Still referring to FIG. 1, in preferred embodiments, the cannula device 100 comprises an attachment member 160 connected to the tubular extension proximal end 121. The attachment member 160 is not limited to a particular position in relation to the tubular extension proximal end 121. In certain embodiments, the attachment member 160 extends outward from the tubular extension proximal end 121 at any desired angle (e.g., 0 to 180 degrees). In preferred embodiments, the attachment member 160 extends outward from the tubular extension proximal end 121 at approximately a 90° angle. The attachment member 160 is not limited to a particular shape (e.g., circual, oval, tabular, triangular, square, diagonal, rectangular, etc.). In preferred embodiments, the shape of the attachment member 160 is a circular protruding lip. The attachment member 160 is not limited to a particular extension length. In preferred embodiments, the extension length of the attachment member 160 is at least 0.1 cm (e.g., at least 0.5 cm, 1 cm . . . 2 cm). In some embodiments, the attachment member 160 has protruding lip fixtures (e.g., edges, lips, tongues, etc.) allowing additional medical instruments (e.g., surgical catheters) to lock onto the cannula device 100 and prevent undesired movement of the medical instrument.

In some embodiments, the attachment member 160 has protruding lip fixtures (e.g., edges, lips, tongues, etc.) allowing frameless stereotactic navigation systems such as StealthStation (Medtronic Navigation, Colorado) or BrainLAB VectorVision (Germany) to lock onto the cannula device 100. Attachment of the navigation system will allow for planning of surgical instrument placement and predict surgical instrument positioning before being passed through the cannula.

Still referring to FIG. 1, in preferred embodiments, as a cannula device 100 is positioned within a bone hole (e.g., burr hole), the attachment member 160 engages and attaches onto the top surface of the bone thereby securing the cannula device 100 within the bone (described in more detail below). In some embodiments, the attachment member 160 attaches onto the top surface of a bone with an adhesive agent (e.g., fibrin glue, cranioplastic cement). In preferred embodiments, the attachment member 160 attaches onto the top surface of a bone with fastening agents (e.g., nails, threaded fasteners).

Still referring to FIG. 1, the attachment member 160 has therein at least one attachment hole 170. In preferred embodiments, the attachment holes 170 are configured to receive threaded fasteners (e.g., screws such as bone screws). In preferred embodiments, as a cannula device 100 is positioned within a bone hole (e.g., burr hole), threaded fasteners are inserted into the attachment holes 170 such that the cannula device 100 is secured into a fixed position within the bone hole. The area of the attachment member that extends beyond the tubule extension proximal end 121 is referred to as the overhang portion 175 of the attachment member. As shown in FIG. 1, the attachment holes 170 are located in this overhang portion 175 of attachment member 160. In some preferred embodiments, the shape of the attachment member 160 is tabular such that the overhang portion 175 only encompasses the area surrounding the attachment holes 170. In other embodiments, the overhang portion extends all the way around, or nearly all the way around, the proximal end of the tubular extension.

Referring again to FIG. 1, the attachment member 160 is not limited to a particular manner of connection with the tubular extension proximal end 121. In some certain embodiments, the attachment member 160 is rigidly connected to the tubular extension proximal end 121 at a predetermined angle (e.g., 0 to 180 degrees) in relation to the tubular extension proximal end 121. In such embodiments, as the cannula device 100 is positioned within a bone hole (e.g., a burr hole) the angle of the attachment member 160 in relation to the tubular extension 110 remains fixed. In other certain embodiments, the attachment member 160 is connected to the tubular extension proximal end 121 in a flexible manner (e.g., via a movable hinge or other flexible component) such that the attachment member is able to assume any desired angle in relation to the tubular extension proximal end 121 (e.g., 0 to 250 degrees). In such embodiments, as a cannula 100 is positioned within a bone hole (e.g., bun hole) the angle of the attachment member 160 in relation to the tubular extension 110 may be adjusted to a desired angle (e.g., upon securing of the attachment member 160 with the bone hole, the tubular extension 110 may be adjusted to any desired angle). In other certain embodiments, the attachment member 160 is connected to the tubular extension proximal end 121 in a loose manner (e.g., via a movable hinge) such that the tubular extension 110 can slide in relation to the attachment member 160.

Still referring to FIG. 1, in some embodiments, the attachment member 160 has protruding lip fixtures (e.g., edges, lips, tongues, etc.) allowing additional medical instruments (e.g., ablative devices, biopsy devices, navigation devices, aspiration devices, imaging devices, etc.) to lock onto the cannula device 100 and prevent undesired movement of the medical instrument.

Figure 2:
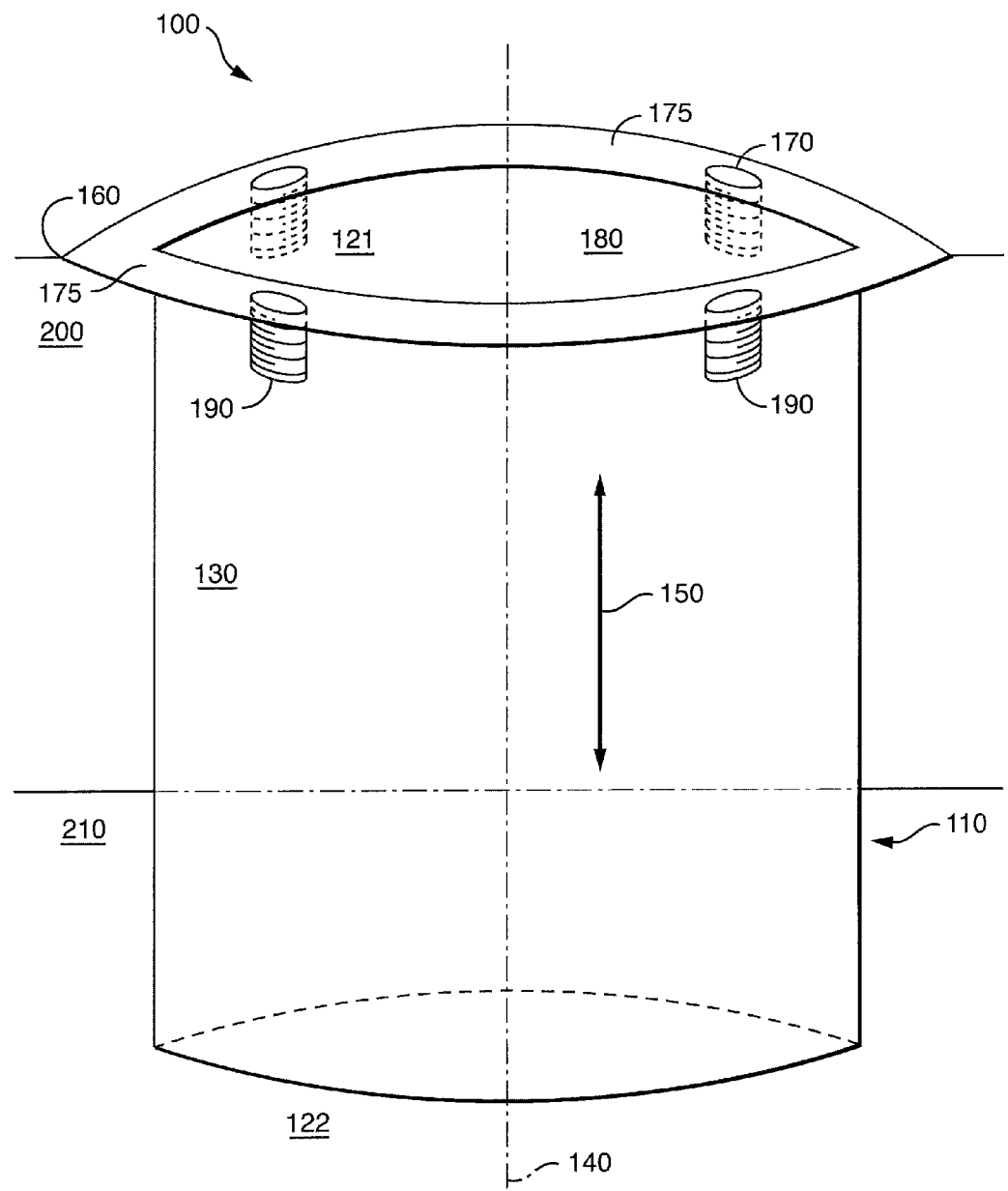
FIG. 2 depicts a cross-sectional side view of a cannula device positioned within a burr hole.

FIG. 2 depicts a cross-sectional side view of a cannula device 100 positioned within a bun hole 180. As shown, the cannula device 100 has a tubular extension 120 with a tubular extension proximal end 121, a tubular extension distal end 122, a tubular extension exterior surface 130, and a longitudinal axis 140. The tubular extension 110 has therein a tubular extension hollow channel 150 running the length of the tubular extension 110 through the tubular extension proximal end 121 and the tubular extension distal end 122. Additionally, the cannula device 100 has an attachment member 160 with four attachment holes 170 positioned within the overhang portion 175. Threaded fasteners 190 are positioned within the attachment holes 170 and the cranium 200 such that the cannula device 100 is secured within the burr hole 180. In addition, the overhang portion 175 is shown extending beyond the tubular extension proximal end 121.

Still referring to FIG. 2, the tubular extension exterior surface 130 is shown engaging the interior sides of the bun hole 180 and the brain 210. As such, in preferred embodiments, the cannula device 100 provides a secure passageway between the outside of the burr hole 180 to an interior region of the brain 210 (e.g., brain stem). The passageway provided by the cannula device 100 provides access to the brain 210 for surgical purposes (e.g., brain tumor biopsy, brain tumor resection, brain tumor imaging, brain tumor treatment, evacuation of brain hematoma, removal of damaged and contused brain tissue, removal of brain infections, etc.) (described in more detail below).

Figure 3:
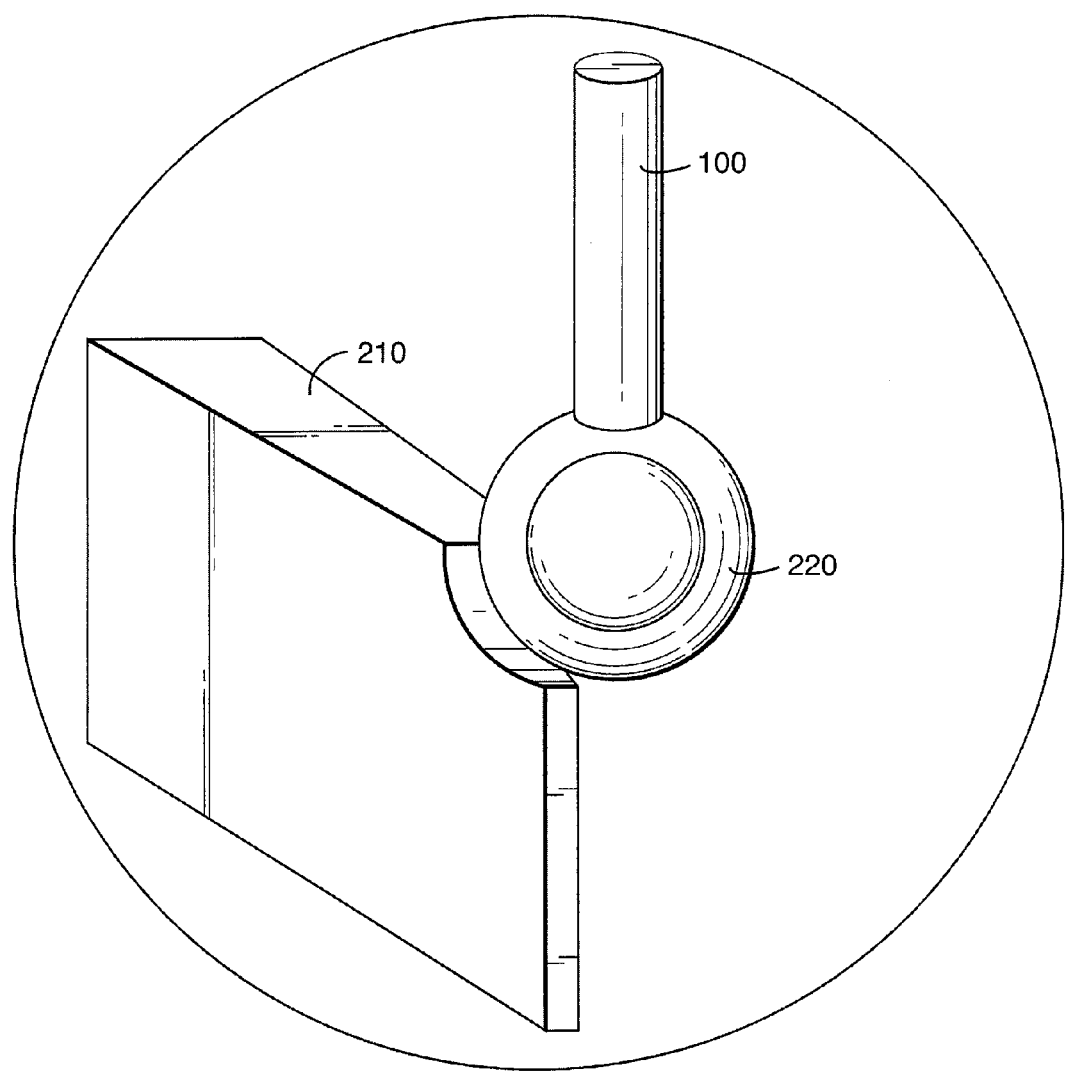
FIG. 3 depicts a cannula device inserted through the brain and onto a brain tumor.

FIG. 3 depicts a cannula device 100 inserted through the brain 210 and onto a region of the brain containing a brain tumor 220. FIG. 3 demonstrates one of the advantages the cannula device 100 provides in a neurosurgical setting. In particular, the cannula device permits a neurosurgeon to obtain a direct opening or passageway from a bun hole, through the brian pia, to the surface of a deeply seated brain tumor. The passageway can be used for many surgical purposes, including but not limited to, administration of medications, and insertion of surgical instruments for treatment purposes (e.g., tumor cauterization, tumor aspiration, tumor biopsy).

Cutting and Cauterizing Device

Figure 4:
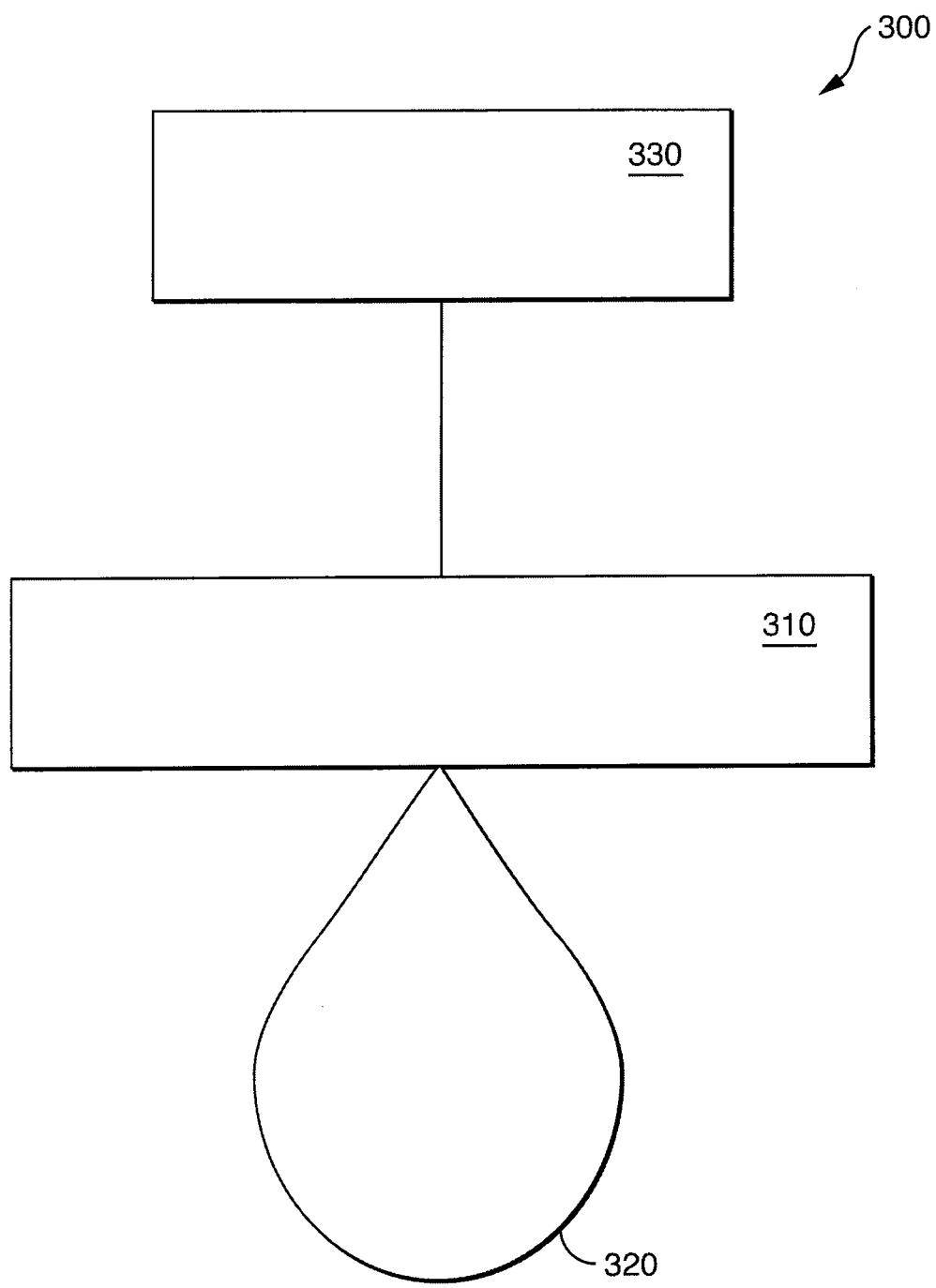
FIG. 4 shows a schematic diagram of a cutting and cauterizing device embodiment of the present invention.

FIG. 4 shows a schematic diagram of a cutting and cauterizing device 300 embodiment of the present invention. In preferred embodiments, the cutting and cauterizing device 300 is configured to cut a tissue (e.g., brain tumor) and cauterize a tissue (e.g., brain tumor) (described in more detail below).

Still referring to FIG. 4, the cutting and cauterizing device 300 generally comprises a cutting and cauterizing device motor 310 connected to at least one cutting and cauterizing device wire 320. In preferred embodiments, the cutting and cauterizing device wire 320 may assume any desired shape (e.g., a linear shape, a curvilinear shape, a circular shape, a zig-zagged shape). The cutting and cauterizing device wire 320 is not limited to a particular length. In preferred embodiments, the length of the cutting and cauterizing device wire 320 is at least 0.25 cm in length (e.g., 0.5 cm in length, 0.75 cm in length, 1 cm in length, 2 cm in length . . . 20 cm in length). The cutting and cauterizing device wire 320 is not limited to a particular diameter measurement. In preferred embodiments, the diameter of the cutting and cauterizing device wire 320 is at least 0.05 mm (e.g., 0.075 mm, 0.01 mm . . . 0.05 mm, etc.). In preferred embodiments, the length, diameter, and shape of the cutting and cauterizing device wire 320 are such that the cutting and cauterizing device wire 320 is able to wrap around a desired tissue (e.g., brain tumor). In particularly preferred embodiments, the cutting and cauterizing device wire 320 is configured to cut through a tissue and cauterize the tissue (described in more detail below).

Still referring to FIG. 4, in preferred embodiments, the cutting and cauterizing device motor 310 is configured to expand and retract the cutting and cauterizing device wire 320. The cutting and cauterizing device motor 310 is not limited to a particular type or size of motor. In preferred embodiments, the size of the cutting and cauterizing device motor 310 is able to fit (e.g., in an expanded or unexpanded form) within the cannula device described above. In preferred embodiments, the cutting and cauterizing device motor 310 is configured to continuously rotate the cutting and cauterizing device wire 320. The cutting and cauterizing device motor 310 is able to continuously rotate the cutting and cauterizing device wire 320 at any desired rotational speed (e.g., at least 0.1 rotations per second, 1 rotation per second, 10 rotations per second, 100 rotations per second, 1000 rotations per second). In preferred embodiments, a continuously rotating cutting and cauterizing device wire 320 is able to cut a tissue (e.g., a brain tumor).

Still referring to FIG. 4, the cutting and cauterizing device 300 comprises a cutting and cauterizing device energy source 330. The cutting and cauterizing device energy source 330 is not limited to a particular type of energy (e.g., electric, radiation, laser). In preferred embodiments, the energy source of the cutting and cauterizing device energy source 330 is electric energy. In preferred embodiments, the cutting and cauterizing device energy source 330 is configured to deliver energy (e.g., electric current energy) to the cutting and cauterizing device wire 320. In preferred embodiments, the cutting and cauterizing device electric energy wire 320 is configured to emit energy received from the cutting and cauterizing device energy source 330. In particularly preferred embodiments, the emission of energy (e.g., electric energy) from the cutting and cauterizing device wire 320 cauterizes a tissue (e.g., a brain tumor).

FIG. 5A-B show a side view of a cutting and cauterizing device 300 secured within a burr hole 180. As shown, the cutting and cauterizing device 300 has a cutting and cauterizing device wire 320. The cutting and cauterizing device wire 320 is shown extending beyond the terminus of the cannula device 100 and onto a brain tumor 220. The cutting and cauterizing device wire 320 is shown assuming the shape of the brain tumor 220. In preferred embodiments, continuous rotation of the cutting and cauterizing device wire 320 allows the cutting of the brain tumor. In preferred embodiments, emission of electric energy through the cutting and cauterizing device wire 320 allows cauterization of the brain tumor.

Still referring to FIG. 5A-B, FIG. 5A shows the cutting and cauterizing device wire 320 within the brain tumor 220. The cutting and cauterizing device 300 is shown rotating. FIG. 5A shows the cutting and cauterizing device wire 320 expanded and taking a circular shape just up to the edge of the tumor 220. FIG. 5B shows a devascularized tumor 220 after the cutting and cauterizing device 300 is removed.

FIG. 6A-C show exemplary shapes the cutting and cauterizing wire 320 may assume. FIG. 6A displays the cutting and cauterizing device wire 320 in a linear shape. FIG. 6B displays the cutting and cauterizing device wire 320 in an oval shape (see, e.g., the arrows indicating the expansion of the cutting and cauterizing device wire 320). FIG. 6C displays the cutting and cauterizing device wire 320 in a circular shape. As such, the cutting and cauterizing device 300 provides a neurosurgeon with a powerful cutting and cauterizing instrument capable of assuming various shapes depending on the particular shape and size of the tissue (e.g., brain tumor). Use of the cannula device and the cutting and cauterizing device together provides a direct passageway and treatment approach for deeply seated tumors (e.g., brain stem tumors).

Aspiration Device

FIGS. 7A and 7B show side views of an aspiration device 400 embodiment of the present invention. The aspiration device 400 generally comprises at least one aspiration device suction arm 410 and an aspiration device suction member 420. The aspiration device 400 is not limited to a particular size. In preferred embodiments, the aspiration device 400 is able to fit within the cannula devices of the present invention. In preferred embodiments, the aspiration device 400 is configured to aspirate a fragmented (e.g., cut) tissue (e.g., brain tumor) (described in more detail below).

Still referring to FIGS. 7A and 7B, the aspiration device suction arm 410 has an aspiration device suction arm open end 430, an aspiration device suction arm closed end 440, and has therein an aspiration device suction arm hollow channel 460. In preferred embodiments, the length of the aspiration device suction arm 410 is at least 1 cm (e.g., at least 1.5 cm, at least 2 cm . . . at least 3 cm). In preferred embodiments, the diameter of the aspiration device suction arm 410 is at least 0.5 cm (e.g., 1 cm, 2 cm . . . 5 cm). The aspiration device suction arm 410 is not limited to a particular shape (e.g., linear, curvilinear, zig-zagged, oval, circular). In preferred embodiments, the aspiration device suction arm 410 is configured to assume any desired shape. In preferred embodiments, the dimensions of the aspiration device suction arm 410 are configured such that the aspiration device suction arm 410 is capable of expanding into the shape of a circle with at least a 1 cm diameter. In preferred embodiments, the aspiration device suction arm 410 is configured to expand or contract in shape. In preferred embodiments, expansion or contraction of the aspiration device suction arm 410 permits the contacting of a tissue (e.g., brain tumor) with the aspiration device 400.

Still referring to FIGS. 7A and 7B, the aspiration device 400 has aspiration device suction openings 450. The aspiration device suction opening 450 is not limited to a particular location within the aspiration device 400. In some embodiments, the aspiration device suction opening 450 is positioned along the aspiration device suction arm 410 (as shown in FIG. 7A). In preferred embodiments, positioning of an aspiration device suction opening 450 along the aspiration device suction arm 410 permits, for example, the contacting of a tissue with the aspiration device suction arm 410 such that the tissue is aspirated through the aspiration device suction opening 450. In other embodiments, the aspiration device suction opening 450 is positioned within the aspiration device suction member 420 (as shown in FIG. 7B). In preferred embodiments, positioning of an aspiration device suction opening 450 along the aspiration device suction member 420 permits, for example, the contacting of a tissue with the aspiration device suction arm 410 such that the tissue is drawn toward the aspiration device suction member 420 where the tissue is aspirated through the aspiration device suction opening 450.

Still referring to FIGS. 7A and 7B, the aspiration device 400 is not limited to a particular number of aspiration device suction openings 450. In preferred embodiments, the aspiration device 400 has at least 1 aspiration device suction opening 450. The aspiration device suction opening 450 is not limited to a particular size. In preferred embodiments, the size of the aspiration device suction opening 450 is such that fragmented tissues are able to flow into the aspiration device suction opening 450. The aspiration device suction opening 450 is not limited to a particular shape (e.g., rectangular, oval, circular, square, triangular, zig-zagged). In preferred embodiments, the shape of the aspiration device suction opening 450 is oval and/or rectangular.

Still referring to FIGS. 7A and 7B, the aspiration device suction member 420 is configured to generate a suction force through the aspiration device suction opening 450. Additionally, the aspiration device suction member 420 is configured to continuously rotate the aspiration device suction arm 410. The aspiration device suction member 420 is not limited to a particular method of operation (e.g., a suction motor, a rotational motor). The aspiration device suction member 420 is configured to provide any desired amount of suction force through the aspiration device suction opening 450. In preferred embodiments, the amount of suction force provided by the aspiration device suction member 420 is sufficient to aspirate a fragmented tissue (e.g., fragmented brain tumor). In preferred embodiments, the aspiration device suction member 420 is configured to continuously rotate the aspiration device suction arm 410 at any desired rotational speed (e.g., at least 0.1 rotations per second, 1 rotation per second, 10 rotations per second, 100 rotations per second, 1000 rotations per second). In preferred embodiments, the aspiration device suction member 420 is configured to continuously rotate the aspiration device suction arm 410 while simultaneously applying a suction force through the aspiration device suction opening 450.

Figure 8A:
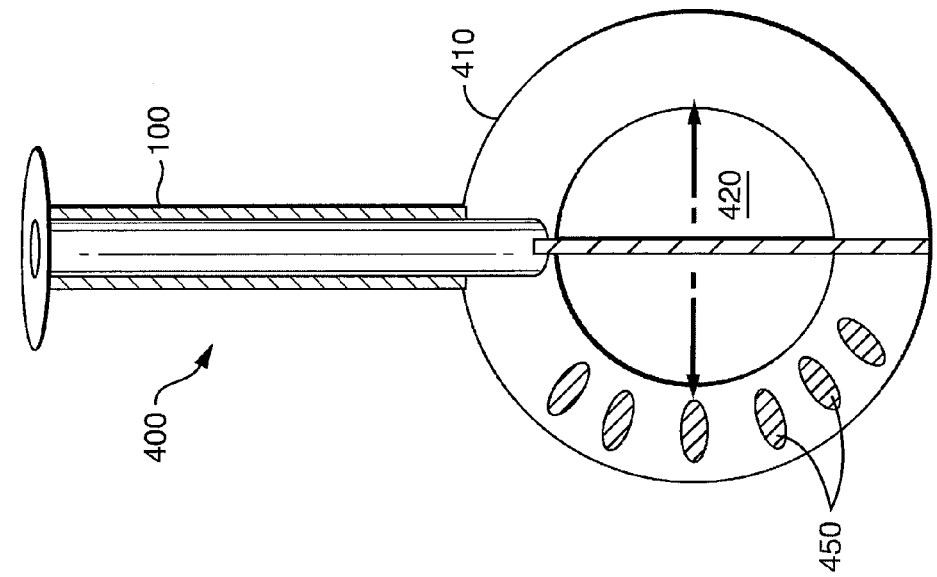
FIGS. 8A-B show an aspiration device positioned within a cannula device.
Figure 8B:
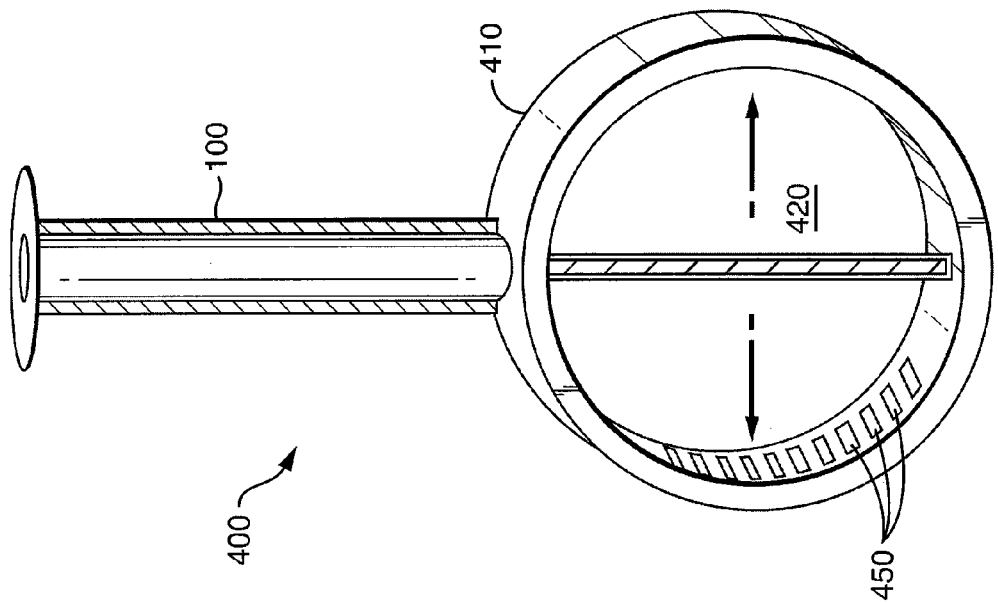

FIGS. 8A and 8B show an aspiration device 400 positioned within a cannula device 100. As shown, the aspiration device 400 has an aspiration device suction member 420 and an aspiration device suction arm 410 having therein aspiration device suction openings 450. In FIG. 8A, the aspiration device suction openings 450 are positioned along the interior of the aspiration device suction arm 410. In FIG. 8B, the aspiration device suction openings 450 are positioned along the exterior of the aspiration device suction arm 410. As shown in FIGS. 8A and 8B, the aspiration device 400 is positioned within the cannula device 100 such that the aspiration device suction member 420 engages the walls of the cannula device 100, and the aspiration device suction arm 410 extends beyond the terminus of the cannula device 100. The shape of the aspiration device suction arm 410 is circular (see, e.g., the arrows indicating the aspiration device suction arm 410 is configured to assume a circular shape).

FIG. 9 shows an aspiration device 400 positioned within a cannula device 100 secured within a bun hole 180. As shown, the aspiration device 400 has an aspiration device suction member 420 and an aspiration device suction arm 410 having therein aspiration device suction openings 450. As shown, the aspiration device 400 is positioned within the cannula device 100 such that the aspiration device suction member 420 engages the walls of the cannula device 100, and the aspiration device suction arm 410 extends beyond the terminus of the cannula 100. The shape of the aspiration device suction arm 410 is circular. In preferred embodiments, the aspiration device 400 is configured such that continuous rotation of the aspiration device suction arm 410 while simultaneously providing a suction force through the aspiration device suction arm 410 permits the aspiration of tissue from a body cavity (e.g., a fragmented brain tumor cavity).

Figure 10:
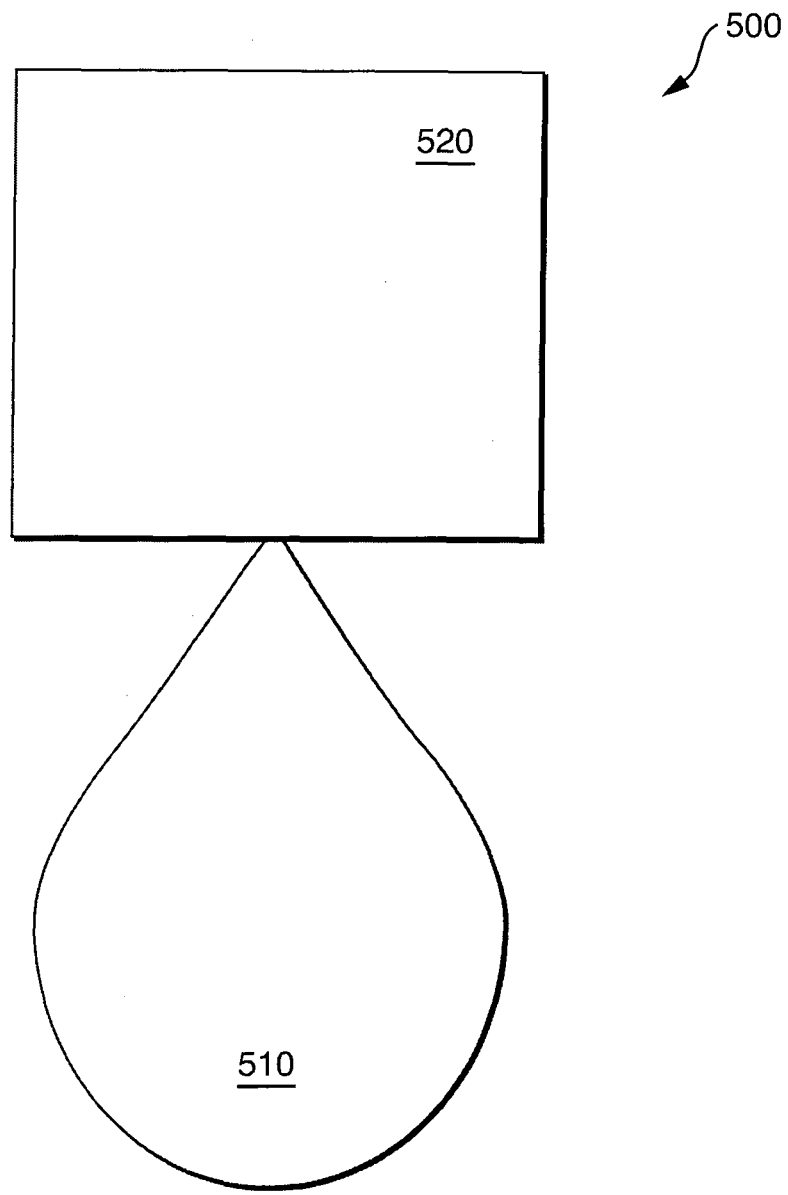
FIG. 10 shows a side view of a hemostasis promoting device embodiment of the present invention.

Still referring to FIG. 9, FIG. 9A shows the aspiration device suction arm 410 positioned around a circumference creating an interior space, which may contain a brain tumor. The arrows indicate the suction force provided through the aspiration device suction openings 450. FIG. 9B shows the aspiration device suction arm 410 rotating around the interior space (e.g., brain tumor, see, e.g., the rotational arrow) while applying a suction force through the aspiration device suction openings 450. FIG. 9B also shows a wire 320 for cutting brain tissue. FIG. 9C shows an aspirated cavity of a brain tumor 220 following application of the aspiration device 400. Use of the cannula devices of the present invention and the aspiration device together provides a direct passageway and aspiration approach for deeply seated tumors (e.g., thalamus tumors) or hematomas Hemostasis Promoting Device FIG. 10 shows a side view of a hemostasis promoting device 500 embodiment of the present invention. The hemostasis promoting device 500 generally comprises a hemostasis member 510 and a expansion member 520. The hemostasis promoting device 500 is not limited to a particular size. In preferred embodiments, the hemostasis promoting device 500 is able to fit within the cannula devise described above. In preferred embodiments, the hemostasis promoting device 500 is able to induce hemostasis within a hemorrhaging body cavity (e.g., a hemorrhaging brain tumor cavity) (described in more detail below).

Still referring to FIG. 10, the hemostasis member 510 is configured for inflation and deflation. The hemostasis member 510 is not limited to a particular material composition (e.g., rubber, plastic, nylon, or mixture thereof). In preferred embodiments, the material composition of the hemostasis member 510 is synthetic rubber. The hemostasis member 510 is not limited to a particular size. The hemostasis member 510 is not limited to a particular shape. In preferred embodiments, the deflated shape of the hemostasis member 510 is shriveled. In preferred embodiments, the inflated shape of the hemostasis member 510 is circular (e.g., inflated balloon shape). In particularly preferred embodiments, upon insertion into a body cavity, the inflated shape of the hemostasis member 510 matches the shape of the body cavity.

Still referring to FIG. 10, the hemostasis member 510 is configured to induce hemostasis upon a hemorrhaging body cavity. The hemostasis member 510 is not limited to a particular method of promoting hemostasis. In some preferred embodiments, the hemostasis member 510 provides direct pressure onto the body cavity thereby promoting hemostasis. In other preferred embodiments, the exterior surface of the hemostasis member 510 contains a hemostasis promoting agent. The present invention is not limited to particular hemostasis promoting agents. In preferred embodiments, hemostasis promoting agent is a thrombogenic agent.

Still referring to FIG. 10, the expansion member 520 is configured to inflate and deflate the hemostasis member 510. The expansion member 520 is not limited to a particular method of inflating and deflating the hemostasis member 510. In some preferred embodiments, the expansion member 520 inflates the hemostasis member 510 by filling it with a gaseous substance (e.g., air). In some preferred embodiments, the expansion member 520 inflates the hemostasis member 510 with a liquid substance (e.g., water, radiolabeled liquid). In preferred embodiments, the expansion member 510 deflates the hemostasis member 510 by removing the inflation agent (e.g., gaseous substance, liquid substance). In particularly preferred embodiments, the expansion member 520 is configured to inflate or deflate the hemostasis member 510 such that it fits a body cavity (e.g., a brain tumor cavity). In preferred embodiments, the expansion membrane has an internal cannula with an open distal end. This opening can allow for injection of solutions such as hemostatic agents or other materials into the cavity. In preferred embodiments, the tip of the hemostasis member 510 may have an opening to allow for aspiration of solutions or other materials from the cavity.

Figure 11:
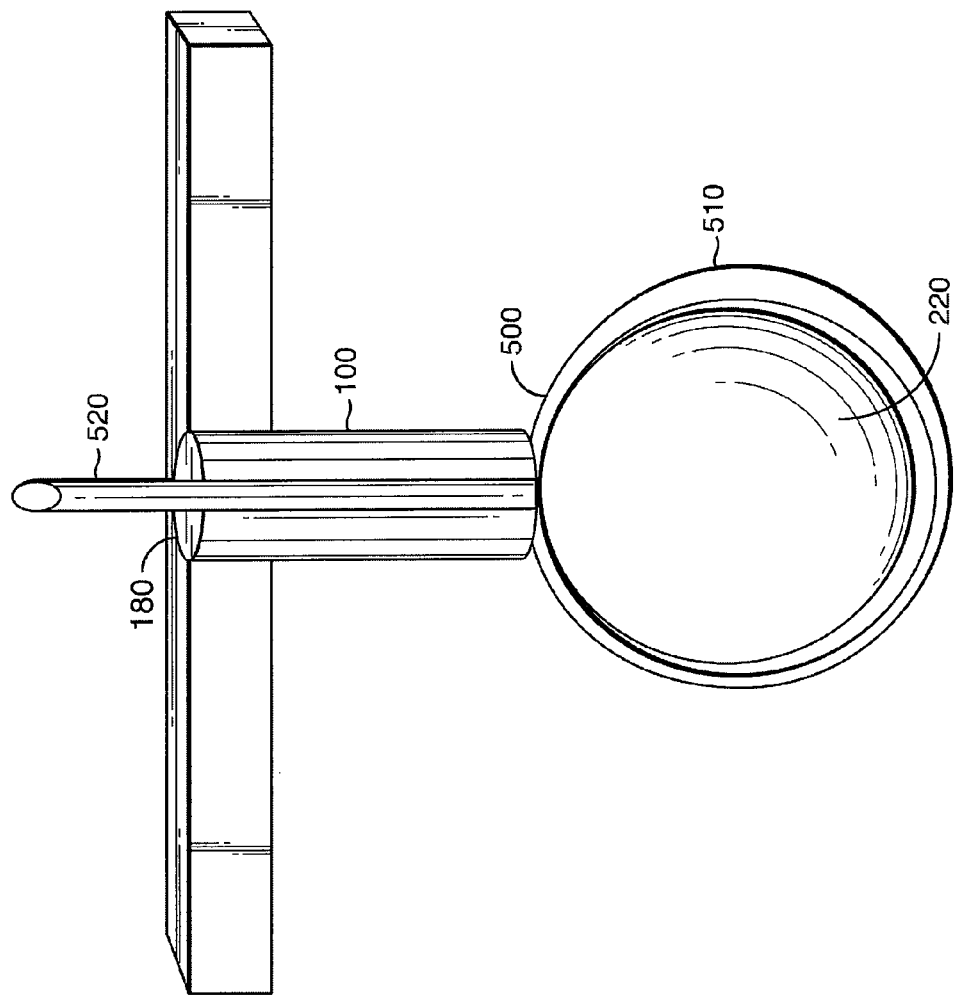
FIG. 11 shows a hemostasis promoting device positioned within a cannula device secured within a bun hole.

FIG. 11 shows a hemostasis promoting device 500 positioned within a cannula device 100 secured within a burr hole 180. As shown, the hemostasis promoting device 500 has an hemostasis member 510 and a expansion member 520. The hemostasis promoting device 520 is positioned within the cannula device 100 such that the expansion member 520 engages the walls of the cannula device 100, and the hemostasis member 510 extends beyond the terminus of the cannula device 100. The hemostasis member 510 is shown in an inflated shape such that it has assumed the shape of the body cavity. The hemostasis member 510 is configured such that hemostasis is induced upon contact with the cavity of the brain tumor 220. Use of the cannula devices of the present invention and the hemostasis promoting device together provides a direct passageway and hemostasis approach for deeply seated tumors (e.g., thalamus tumors).

Wire Containing Probe Devices and Exemplary Methods

The present invention provides wire (loop) containing probe devices and methods for employing such devices. The instrument probe allows, for example, for removal of intracerebral hematomas, and brain tumors, through a small burr hole 680. The probe instrument described below may be inserted through a cannula which is introduced up to the surface of the lesion using currently available navigation systems. The probe device is then passed through this port to disconnect, cauterize, fragment and/or aspirate the hematoma (or tumor tissue).

Figure 12:
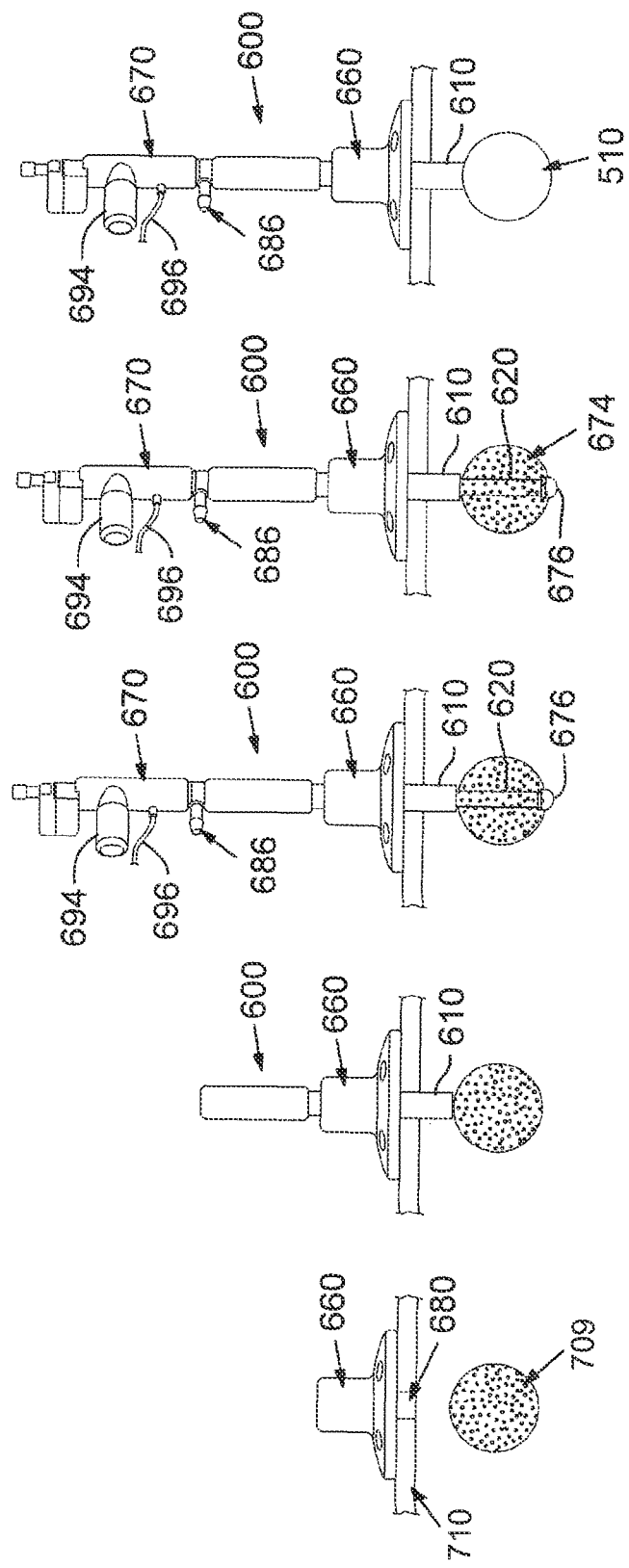
FIG. 12 shows pictorially one embodiment of the steps that can be taken to treat a hematoma or tumor using a probe device and related components.

One exemplary embodiment employing the probe (described in more detail below) is depicted in FIG. 12 and is described as follows:

1) A standard bun hole 680 measuring 7-14 mm in diameter is created. The mounting mechanism fixture 660 is secured in place to the skull 710. The mounting system shown in FIG. 12 is exemplary. In certain embodiments, the mounting mechanism is designed based on specifics of the probe design and navigation system, and will pivot and can even be secured with a robotic arm.

2) A Cannula 600, that will provide access to the brain mass and allow for passage of subsequent instruments, is inserted next. This cannula (e.g., diameter: 0.5-1 cm; length 2-5 cm) may have a stylet which will be removed after insertion and may be made of advanced engineered polymers such as PEEK known for its high strength and bio-compatibility. A Cannula can be inserted using image guidance techniques (such as Stealth or BrainLab) up to the edge of the mass and tubular extension 610 will act as channel for passage of subsequent devices.

3) The probe 670 (with cutting wires 674) is introduced next through the cannula and is used for separation, fragmentation, and aspiration of the mass 709 (i.e. tumor, lesion or hematoma, for example) from surrounding brain tissue. The tip 676 of the probe extends through the lesion to the other surface of the lesion before locking into place. The probe has a central stem 620 containing a rotating shaft (FIGS. 17 and 18) that has multiple wires (loops/prongs 674) that will expand and conform into a circle (or other shapes). These conductive (metallic) wires can connect to a radio-frequency (RF) source (FIG. 13) and can extend within the hematoma, or beyond the edge of the tumor, to allow for disconnection of the mass from surrounding hematoma or gliotic margin (in case of tumors) using RF energy.

4) The Probe shaft 620 is retracted and a balloon 510 is introduced next. The balloon is used for hemostasis and tamponade of small bleeding vessel. This balloon-type device is inserted through the cannula and inflated to the appropriate volume to expand and completely fill the cavity. Pressure from the balloon is sufficient to occlude small arterioles. Furthermore, the center of this device may have a hollow catheter for injection of thrombogenic agents such as thrombin, which will flow over the surface of the balloon to promote hemostasis. The same central catheter is used for aspiration of the cavity contents, after the balloon has been deflated. It is also connected to a pressure transducer to monitor intracranial pressure.

Figure 13:
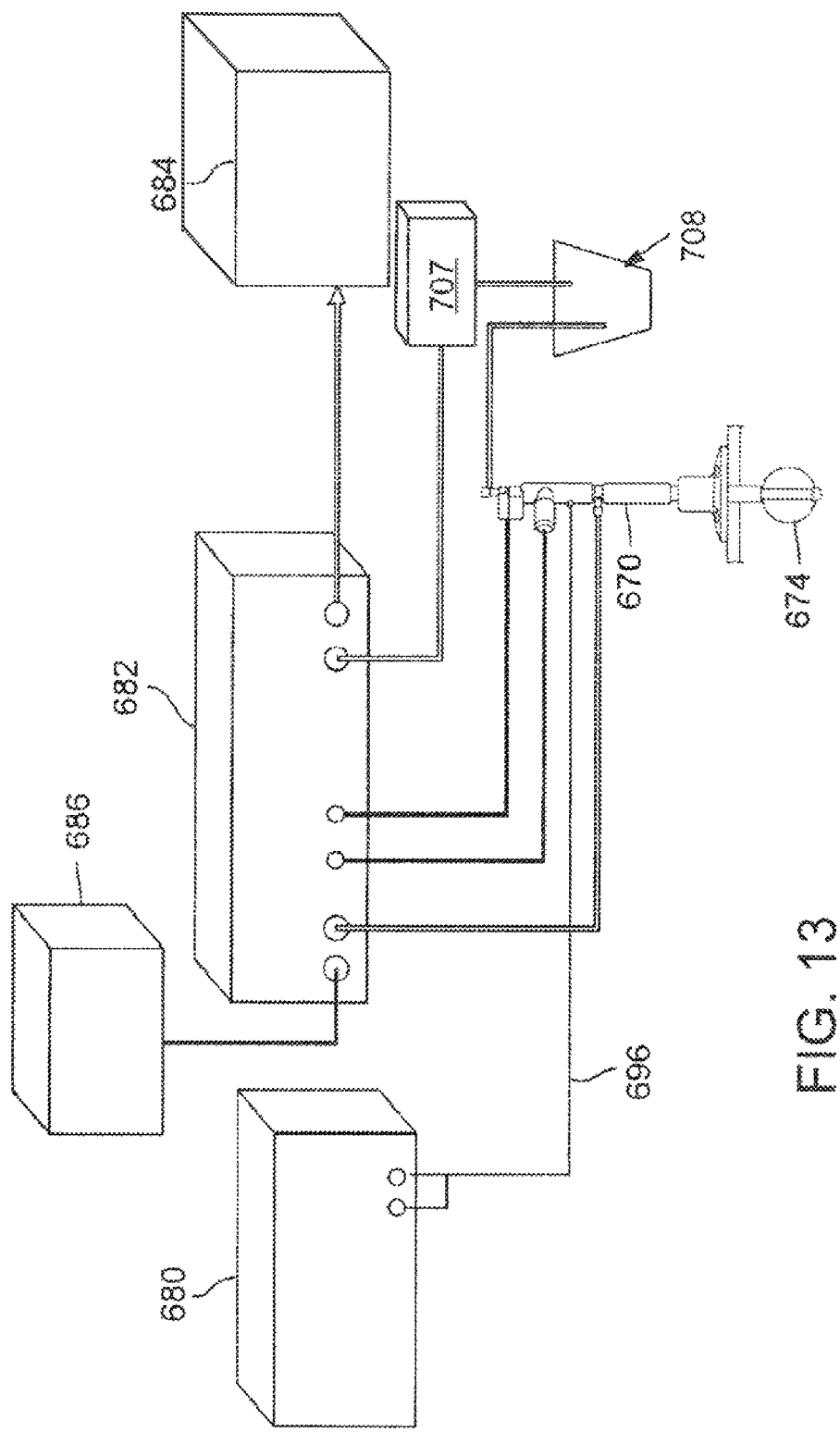
FIG. 13 shows one embodiment of the systems of the present invention including a loop/wire containing probe, an RF generator component, an irrigation supply component, and a controller component.
Figure 14:
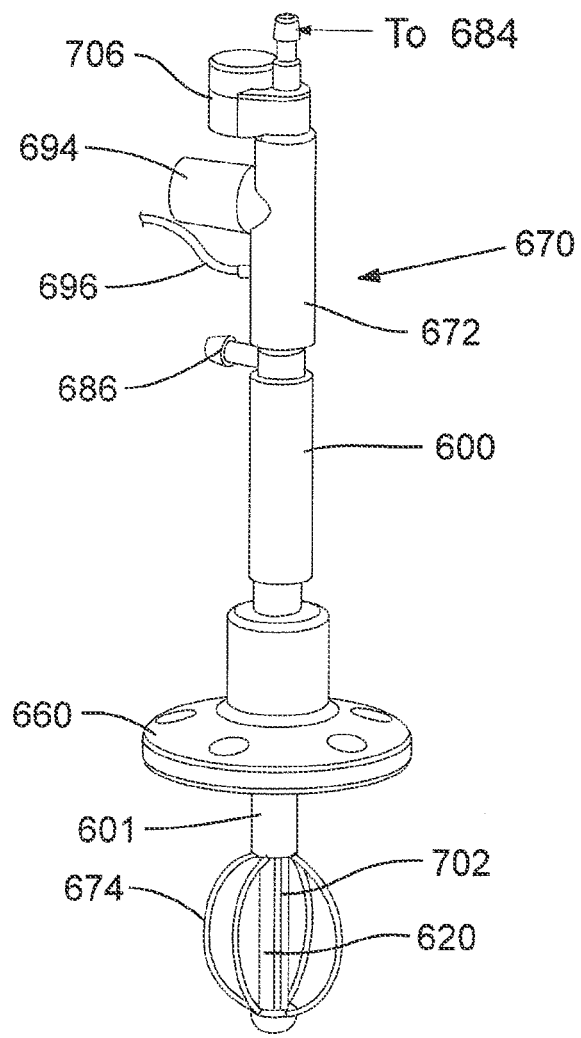
FIG. 14 shows one embodiment of the loop/wire containing probe device of the present invention.

The present invention provides systems that include the wire containing probe 670 and a probe actuating subsystem described below. An exemplary system is shown in FIG. 13. The various components of the system are described below.

Probe Device

Figure 15:
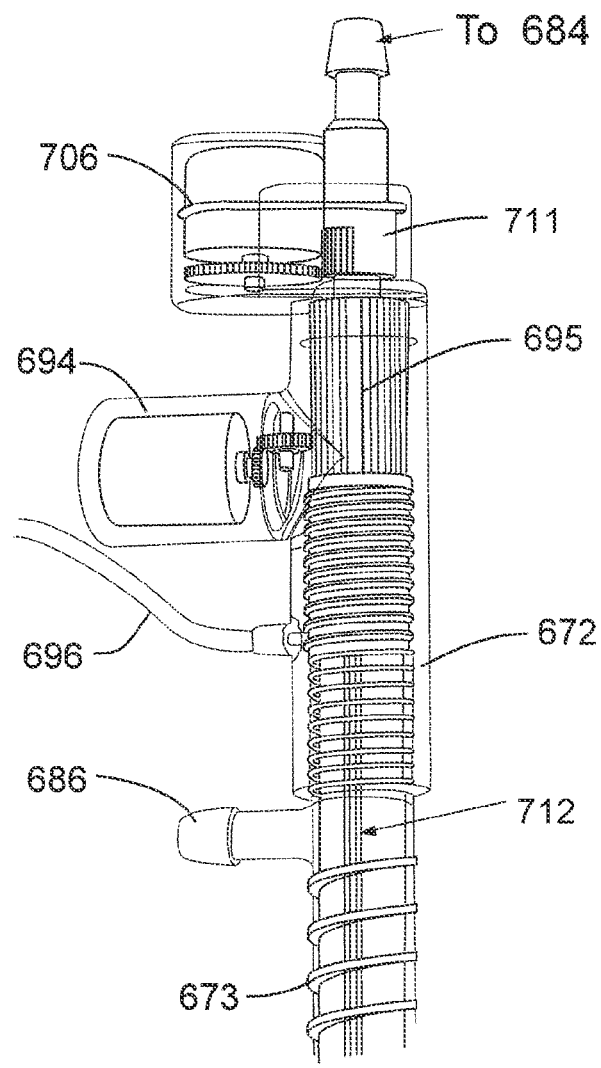
FIG. 15 shows one embodiment of the proximal end of a probe device.

The probe 670 is the device that may be inserted through the cannula to cut, fragment, cauterize and/or aspirate the mass. An exemplary embodiment is shown in FIGS. 14-17 with reference to FIG. 13. The embodiments described below are in reference to FIGS. 14-17 and are merely exemplary. The four expanding loops (wires 674) are connected to the central stem 620 at the distal end 676 and are pushed from their resting state into loops by a motorized loop expander mechanism 694 mounted on the probe outer sleeve 672. The proximal ends of these loops 712 are connected to the RF generator 680 via connection 696 (FIGS. 13 and 15). The central stem 620 of the probe contains the suction channel or slot 702 and the slotted cutting tube 704 (see FIGS. 14 and 16). The proximal end of this inner suction tube is connected to the controller 682 (FIG. 13) and thru switching valves to the vacuum source 684 (FIG. 13). The filter 707 is connected to the controller 682 and to a tissue collection container 708 (FIG. 13). Through the controller's switching valve mechanism, the irrigation fluid from irrigation supply 686 (FIG. 13) is channeled thru the central stem and delivered to the region. The proximal section of the probe is also coupled to a motorized loop expander and rotation mechanism 694. The expansion of the loops can be synchronized with rotation of the probe as well as with the application of the RF energy via RF connection 696. This provides for cutting, cauterizing and fragmentation of the mass simultaneously. The probe mechanism is secured in its position thru attachment to the navigation/guidance mount sub-system 660. The cannula 600 can also be inserted and secured with a robotic arm. The proximal ends of the loops may be securely connected to an Elevator mechanism 695 (FIG. 15).

The motorized loop expander and rotation mechanism 694 is gear coupled to the vertical gear section of the elevator (FIG. 15). The horizontal gear section of the elevator is also coupled to inner horizontal gears of the probe outer sleeve. The rotation of the motorized loop expander and rotation mechanism 694 rotates the elevator which causes the probes to be pushed down resulting in their expansion since the loops are swivel-fixed to the distal end 676 of the probe. The elevator also rotates as it moves down, resulting in simultaneous rotation of the probe and its loops. The RF power 696 is coupled to the metallic elevator 695 as shown in FIG. 15, and therefore, to the loops 674. The probe outer sleeve 672 is plastic and acts as the electrical insulation between the loops and inner cutting tube as well as providing for external isolation for the surgeon and brain tissue. The irrigation fluid from supply 686 is pumped in and delivered to the region through inner vertical channels of the probe sleeve. This results in cut, coagulation and fragmentation of the target tissue. Once the loops are expanded to the target diameter (e.g., as determined in pre-op planning using CT or MR scan images) the motorized action is ceased. The loops are held in expanded position and will serve as hold-back mechanism to keep the tissue edges in place while the fragmented mass is aspirated. This avoids inadvertent collapse of the cavity when the suction mechanism is activated.

Figure 16:
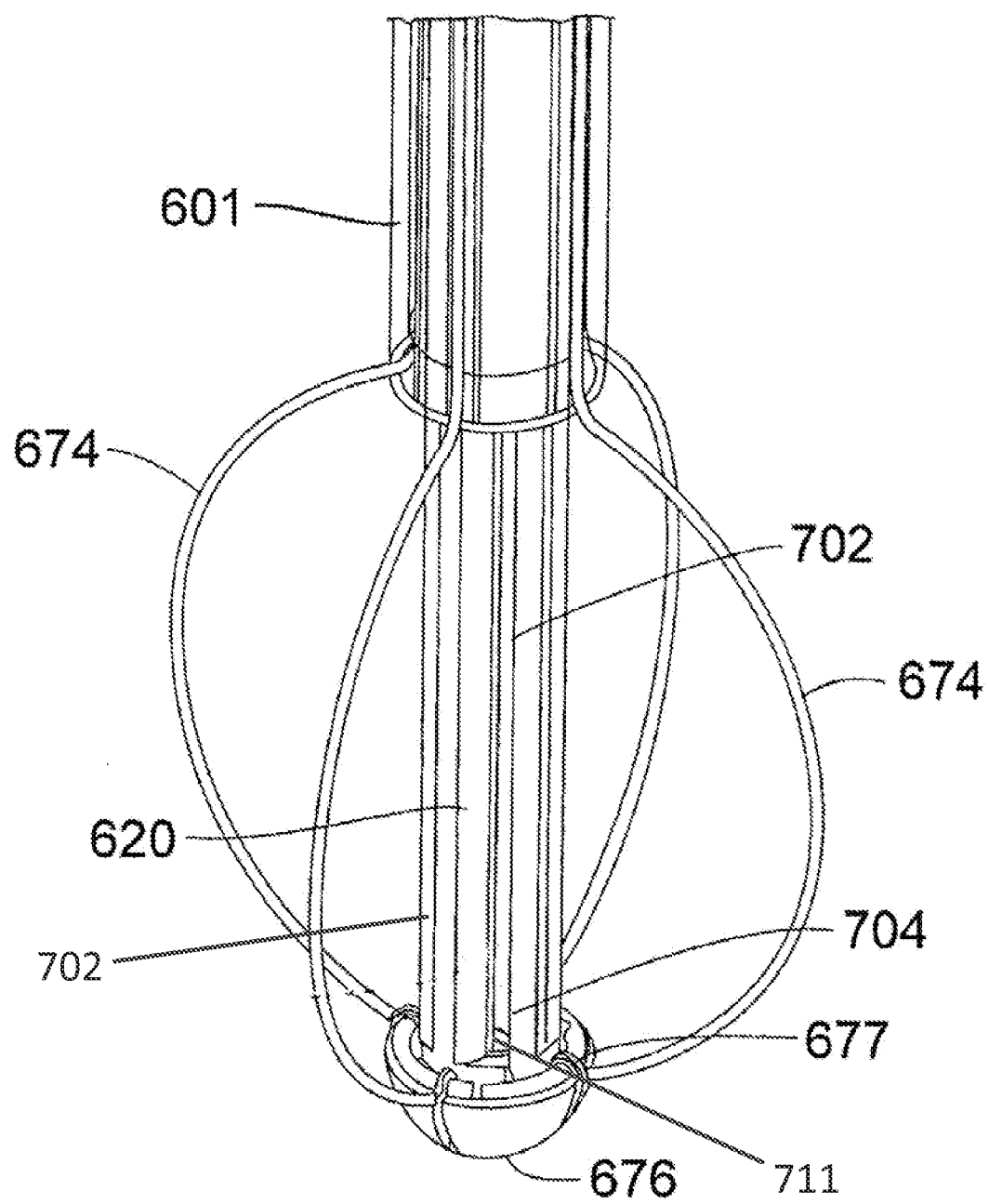
FIG. 16 shows one embodiment of the distal end of a probe device.

The cutting motor is gear-coupled to the gears on the inner cutting tube's 711 proximal end. The aspiration of fragmented mass is next accomplished by rotation of the inner cutting tube 711 inside the probe sleeve while the system controller synchronously applied suction and irrigation fluid (FIGS. 15 and 16). The loops may be made from Nitinol wire and can be secured and fixed to the distal tip 676 via a loop swivel attachment 677 free to swivel and pivot when their proximal end is pushed down by the elevator mechanism 695. The hematomas or tumor mass 709 (FIG. 12) is pulled into the suction slot 702 upon application of vacuum when both the probe sleeve and the inner cutting tube slots 704 are lined up. The rotation by cutting motor mechanism 706 of the inner cutting tube's 711 slots 704 with respect to stationary probe sleeve's slots 702 severs the tissue already pulled into the tube (side-cutting action). The smaller fragments of the tissue are aspirated without the need for cutting action, but with the help of irrigation fluid. Finally, the rotational collapse of the loop 674, while aspiration in progress, also helps move the mass toward the central stem and suction slots.

Figure 17:
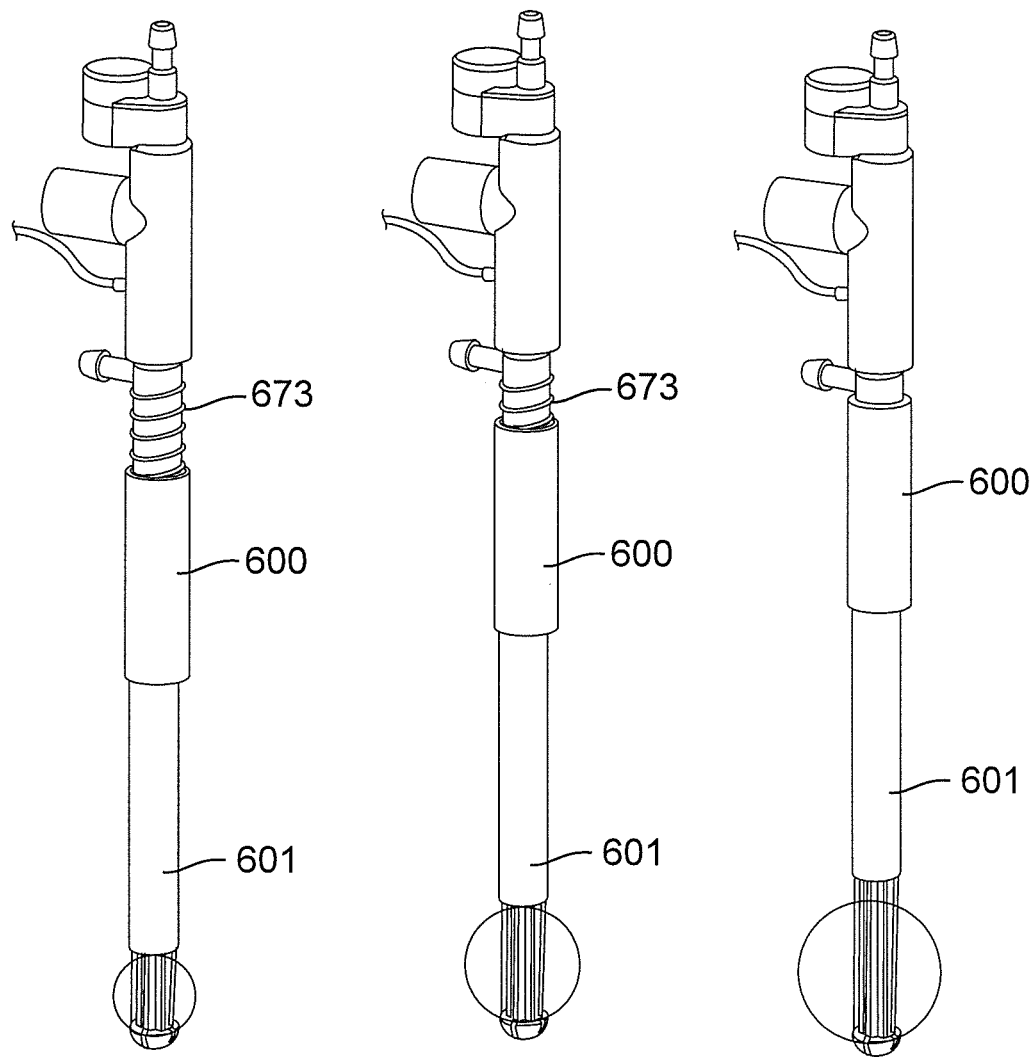
FIG. 17 shows an exemplary side view of probe device illustrating the adjustable loop size. In certain embodiments, the expanded diameter of the loops is set by the probe extension past the distal end of the cannula. In certain embodiments, the probe sleeve's external threading interlocks with the cannula threading to set the diameter of the loops.
Figure 18A:
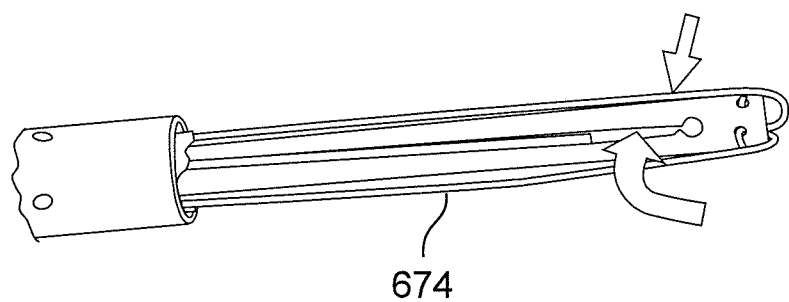
Figure 18B:
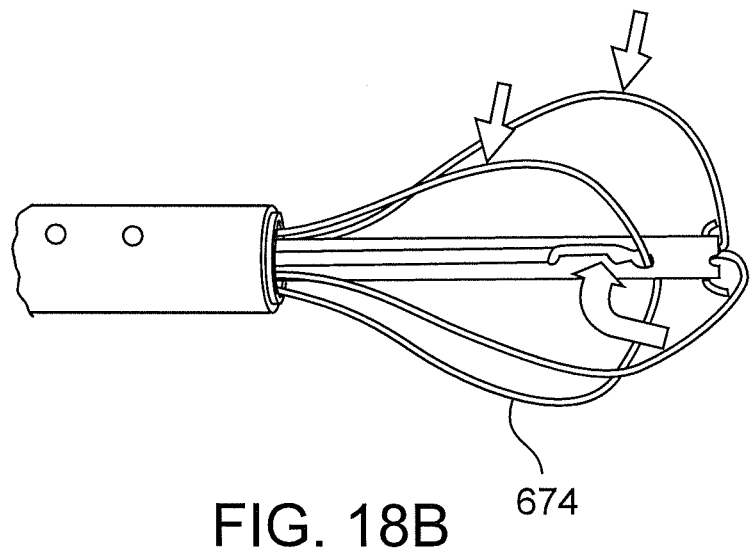
FIG. 18B shows the 4 loops in the expanded position. The curved arrows in the figure show elongated slots (evacuation ports) in the central stem. The evacuation ports, via the central stem, may be linked to vacuum and/or irrigation sources.

The expanded diameter of the loops is set by probe extension past the distal end 601 of the cannula 600. The cannula's distal end is positioned at the edge of the target mass. The probe sleeve's external threading 673 interlocks with the cannula internal threading to set this diameter (FIG. 17). Once the loops are fully collapsed into their initial position, then the probe could be retracted. The balloon can now be inserted to start the next phase as described earlier.

Controller

In some embodiments, the systems of the present invention contain a controller 682. An exemplary controller is described as follows. The controller inter-connects the probe, RF generator, irrigation supply and vacuum source. It contains the electronic as well as electro-pneumatic interfaces and controlling mechanism to facilitate cutting, cauterizing, fragmenting and aspirating the mass. Different modes and sequences of operation are selected thru its front panel controls by a surgeon. It also contains a pressure transducer to measure and control the intracranial pressure.

RF Generator

In some embodiments, the systems of the present invention contain an RF generator 680 or other energy type generator. An exemplary RF generator is manufactured by PEAK Surgical (Palo Alto, Calif.). The PULSAR® generator supplies short pulsed electrical discharges and allows the Probe to cut at much lower average temperatures than conventional electrosurgery without sticking.

Guidance/Navigation

In some embodiments, the systems of the present invention contain a gudance/navigation component. The device placement may be aided by an off-the-shelf navigation/guidance system such as STEALTH or BRAINLAB.

Alternative Embodiments

The present invention is not limited to the cannula device, cutting and cauterizing device, aspiration device, and hemostasis promoting device embodiments described above and as shown in the figures. It is contemplated that devices may be provided that are combinations of the devices of the present invention. For example, the cutting and cauterizing device and aspiration device may be combined into one device. The cutting and cauterizing device and hemostasis promoting device may be combined into one device. The aspiration device and hemostasis promoting device may be combined into one device. The cutting and cauterizing device, aspiration device, and hemostasis promoting device may be combined into one device. Additionally, the cutting and cauterizing device may be combine with both the aspiration device and the hemostasis promoting device.

In preferred embodiments, it is contemplated that any kind of surgical instrument may be used with the cannula devices of the present invention. For example, buttoned probes, ablation devices (e.g., laser ablation devices, cryo-ablation devices, electrical ablation devices, radio-frequency ablation devices, ultrasound ablation devices, thermal ablation devices), imaging devices (e.g., endoscopic devices, stereotactic computer assisted neurosurgical navigation devices, and intraoperative magnetic resonance imaging), implanted deep-brain stimulation (DBS) systems and spinal cord stimulation systems, vessel dilators, curettes, scoops, dissectors, micro forceps, suture tying forceps, ligature guides and carriers, ligature needles, micro needle holders, nerve and vessel hooks, raspatories, rhoton needles, micro scissors, tissue claws, vessel clips, vessel claws, vessel spreaders, brain spatulas, bulldog clamps, chisels, drills, tumor grasping forceps, galea hooks, magnifying glasses, puncture needles, rongeurs may all be used with the cannula devices of the present invention in some embodiments of the present invention.

It is contemplated that the devices of the present invention may be combined within various system embodiments. For example, the present invention contemplates a system comprising the cannula device and any surgical instrument (e.g., ablative device (see, e.g., U.S. Pat. No. 5,554,110; herein incorporated by reference in its entirety), imaging devices (see, e.g., U.S. Pat. Nos. 6,817,976 and 5,697,949; each herein incorporated by reference in their entireties), resectoscope devices (see, e.g., U.S. Pat. No. 6,824,544; herein incorporated by reference in its entirety); the cutting and cauterizing devices of the present invention, ultrasonic tissue resectors (see, e.g., U.S. Pat. No. 5,772,627; herein incorporated by reference in its entirety), endoscopic electric cautery devices (see, e.g., U.S. Pat. No. 6,086,583; herein incorporated by reference in its entirety), cerebral surgery apparatuses (see, e.g., U.S. Pat. No. 5,154,723; herein incorporated by reference in its entirety); pressure hemostatic devices (see, e.g., Japanese Patent Abstact No. 2004223032; herein incorporated by reference in its entirety), the aspiration devices of the present invention, the hemostasis promoting devices of the present invention, and/or any combinations thereof) positioned within the cannula device.

Additionally, it is contemplated that the devices of the present invention may be combined within various kit embodiments. For example, the present invention contemplates kits comprising the cannula device along with any one or more accessory agents. The present invention is not limited to any particular accessory agent. For example, accessory agents include but are not limited to ablation devices, imaging devices, resection devices (e.g., the cutting and cauterizing device of the present invention), aspiration devices (e.g., the aspiration device of the present invention), hemostasis promoting devices (e.g., the hemostasis promoting device of the present invention), and/or any combinations thereof. Additionally, the present invention contemplates kits comprising instructions (e.g., surgical instructions, pharmaceutical instructions) along with the cannula device of the present invention along with a pharmaceutical agent (e.g., a neurological medication).

Additionally, it is contemplated that the devices of the present invention may be combined within various kits or system embodiments. For example, the kits or systems may comprise a device comprising a cannula member, and a device comprising a cutting and cauterizing member, an aspiration member, and a hemostasis member. In preferred embodiments, the kit or system comprises a device comprising a cannula member, a device comprising a cutting and cauterizing member, a device comprising an aspiration member, and a device comprising a hemostasis member. In preferred embodiments, the kit or system comprises a device comprising a cannula member, a device comprising a cutting and cauterizing member, and a device comprising an aspiration member. In preferred embodiments, the kit or system comprises a device comprising a cannula member, a device comprising a cutting and cauterizing member, and a device comprising a hemostasis member. In preferred embodiments, the kit or system comprises a device comprising a cannula member, a device comprising an aspiration member, and a device comprising a hemostasis member. In preferred embodiments, the kit or system comprises a device comprising a cutting and cauterizing member and an aspiration member. In preferred embodiments, the kit or system comprises a device comprising an aspiration member and a hemostasis member. In preferred embodiments, the kit or system comprises a device comprising a cutting and cauterizing member and a hemostasis member. In preferred embodiments, the kit or system comprises a device comprising a cutting and cauterizing member and an aspiration member, and a device comprising a hemostasis member. In preferred embodiments, the kit or system comprises a device comprising an aspiration member and a hemostasis member, and a device comprising a cutting and cauterizing member. In preferred embodiments, the kit or system comprises a device comprising a cutting and cauterizing member and a hemostasis member, and a device comprising an aspiration member. In preferred embodiments, the kit or system comprises a device comprising a cutting and cauterizing member, an aspiration member, and a hemostasis member. In preferred embodiments, the kit or system comprises a device comprising a cutting and cauterizing member, a device comprising an aspiration member, and a device comprising a hemostasis member. In preferred embodiments, the kit or system comprises a device comprising a cutting and cauterizing member, and a device comprising an aspiration member. In preferred embodiments, the kit or system comprises a device comprising a cutting and cauterizing member, and a device comprising a hemostasis member. In preferred embodiments, the kit or system comprises a device comprising an aspiration member, and a device comprising a hemostasis member.

Uses

The devices of the present invention provide numerous advantages over the prior art. Generally, the surgical procedure for the removal of a tissue mass (e.g., a brain tumor) involves a large incision on a subject's head followed by the removal of a piece of cranium. The brain is next uncovered by cutting the dura matter and ultimately the removal of the tissue mass through openings in the brain (e.g., pia). For large tumors that contact the surface of a brain, surgically creating a large opening in the pia is necessary. For deeply seated brain tumors, however, surgically creating a large opening in the pia extending to a deeply seated area presents an enormous risk to the subject (e.g., risk of brain damage). As such, accessing deeply seated brain tumors requires the surgical creation of small and narrow brain openings so as to avoid potential brain damage.

The devices of the present invention overcome this limitation within the prior art. In particular, the cannula device of the present invention provides a secured small and narrow opening from an opening in the cranium (e.g., burr hole) through the brain to a deeply seated area. The cannula may be secured in place to allow multiple different tools to readily access a specific region of the brain to be treated.

The devices of the present invention may be used in any surgical or neurosurgical technique (e.g., surgical method). In preferred embodiments, the devices of the present invention may be used to treat (e.g., excise, aspirate, cut, biopsy, image, cauterize, ablate) brain tumors, unwanted brain masses, hematomas, infracted or damaged brain tissue, infections and unwanted brain lesions. The present invention is not limited to the treatment of a specific type of brain tumor. Indeed, any type of brain tumor may be treated with the devices of the present invention, including but not limited to metastatic brain tumors, astrocytoma tumors, glioma tumors, atypical teratoid/rhabdoid tumors, brain stem gliomas, choroid plexus tumors, craniopharyngiomas, ependymoma tumors, ganglioglioma tumors, germ cell tumors, gliomatosis cerbri tumors, infant brain tumors, medulloblastoma tumors, oligodendroglioma tumors, and optic pathway tumors. Additionally, as the devices of the present invention are not limited to neurosurgical applications, the devices of the present invention may be used to treat (e.g., excise, aspirate, cut, image, cauterize, ablate) tumors, unwanted tissue masses, and unwanted tissue lesions located at any location within a body (e.g., liver, spinal cord, heart, lungs, bones, etc.).

It is also contemplated the devices of the present invention may be used as a form of treatment for diseases and disorders (e.g., brain cancer, aneurysm, strokes, brain trauma). In some preferred embodiments, it is contemplated the devices of the present invention may be used to deliver pharmaceutical agents to locations within a body (e.g., the brain). In some preferred embodiments, it is contemplated the devices of the present invention may be used to deliver therapeutic agents or tissue such as stem cells or immune cells to locations within a body (e.g., the brain).

EXAMPLE

This example describes a contemplated surgical method for removing a deeply seated brain tumor utilizing the devices of the present invention. While this example describes the excision of a brain tumor, the technique may be applied to any unwanted brain mass or unwanted brain lesion. First, a burr hole is placed within the cranium. Second, one of the cannula devices of the present invention is secured within the bun hole (see, e.g., FIGS. 1-3). The cannula device provides a small and narrow passageway leading directly to the surface of the brain tumor. Additionally, the cannula device provides a point of access for the insertion of surgical instruments. Third, tumor biopsy instruments are passed through the cannula device and a biopsy of the brain tumor is completed. Fourth, tumor fragmentation instruments (e.g., ablation instruments) are passed through the cannula device and the brain tumor is fragmented. Fifth, one of the cutting and cauterizing devices of the present invention is passed through the cannula device, the brain tumor is cut from the surrounding brain tissue, and the brain tumor surface cauterized (see, e.g., FIGS. 4-6). Sixth, one of the aspiration devices of the present invention is passed through the cannula device and the fragmented brain tumor is aspirated (see, e.g., FIGS. 7-9). Seventh, one of the hemostasis promoting devices is passed through the cannula device and hemostasis is induced upon the surrounding brain tissue (see, e.g., FIGS. 10-11).

All publications and patents mentioned in the above specification are herein incorporated by reference. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

I claim:

1. A brain probe device for use in removing a lesion from a brain of a patient, the brain probe device comprising:
   a) a cannula having a proximal end and a distal end with a cannula axis therebetween, the cannula including a tubular extension adjacent the distal end, the tubular extension configured for insertion through a craniotomy in a skull of a patient and having a lumen therethrough, the cannula also including an attachment body proximally of and extending radially outwardly from the tubular extension, the attachment body having affixation features configured for affixing the cannula to the skull so as to maintain alignment of the cannula axis with the lesion;

b) a tubular central stem advanceable axially within the lumen of the cannula, wherein said tubular central stem comprises a proximal portion, a distal portion, and a distal end, wherein a plurality of tissue removal openings are formed in a first tube of the tubular central stem along said distal portion, wherein said tubular central stem includes a second tube rotatably aligned with the first tube of the tubular central stem and having radial openings configured to cooperate with the plurality of tissue removal openings so that the second tube provides a rotating side cutter configured to allow cutting of tissue with said plurality of tissue removal openings, and allow aspiration of said tissue through said plurality of tissue removal openings;

c) a probe sleeve, wherein said probe sleeve comprises a proximal portion, and a distal portion, wherein said proximal portion encloses most or all of said proximal portion of said tubular central stem;

d) a plurality of wire loops, wherein each of the plurality of wire loops is operably attached to said distal end of said tubular central stem and configured to be outwardly expanded from said tubular central stem from a contracted configuration to a preset expanded configuration the brain probe device being adjustable such that the preset expanded configuration can be selected from a plurality of expanded configurations, each of the plurality of expanded configurations having a different amount of expansion of the plurality of wire loops from the tubular central stem beyond which further expansion of the plurality of wire loops from the tubular central stem is blocked for the respective preset expanded configuration, and wherein said plurality of wire loops is:
  i) configured for cutting the tissue for subsequent removal via the tubular central stem,
  ii) configured for rotating around said distal portion of said tubular central stem so as to cut the tissue rotationally from the lesion about the cannula axis for subsequent removal via the tubular central stem, and
  iii) configured to be outwardly expanded from the contracted configuration to the preset expanded configuration and contracted from the preset expanded configuration to the contracted configuration so as enable cutting of a desired volume of the tissue corresponding to a size of the lesion for subsequent removal via the tubular central stem;

(e) a loop expander and rotation motor mechanism which is operably linked to said plurality of wire loops and configured to cause rotation and outward expansion of said plurality of wire loops from the contracted configuration to the preset expanded configuration, wherein said loop expander and rotation motor mechanism is located in said probe sleeve, the loop expander and rotation motor mechanism being mounted on the proximal portion of the probe sleeve, the tubular central stem proximal portion including a spline-shaped elevator mechanism inside the probe sleeve, and wherein a first gear interconnects the loop expander and rotation motor mechanism and the elevator mechanism to enable rotation of the tubular central stem while permitting movement of the tubular central stem lengthwise within the probe sleeve;

(f) a rotational cutting motor mechanism attached to said tubular central stem to rotate the rotating side cutter independently of the loop expander and rotation motor mechanism, the rotational cutting motor mechanism including a rotational motor mounted on the proximal portion of the tubular central stem and a second gear interconnecting the rotational motor and the rotating side cutter to rotate the rotating side cutter independently of the loop expander and rotation motor mechanism and movement of the tubular central stem lengthwise within the probe sleeve; and (g) an irrigation lumen configured for transferring irrigation fluid to irrigate said tissue in synchrony with aspiration of said tissue.

2. The brain probe device of claim 1, wherein each of the plurality of the wire loops has a proximal portion and a distal portion, and wherein said loop expander and rotation motor mechanism is configured to controllably displace said proximal portion of each of the plurality of the wire loops distally so as to enable-outward expansion of said plurality of wire loops from the contracted configuration to the preset expanded configuration.

3. The brain probe device of claim 1, further comprising an energy generator connection, wherein said energy generator connection is attached to said probe sleeve.

4. The brain probe device of claim 1, further comprising an irrigation fluid input port, wherein said irrigation fluid input port is attached to said probe sleeve and the probe sleeve includes the irrigation lumen.

5. The brain probe device of claim 1, further comprising a vacuum port connection, wherein said vacuum port connection is attached to said proximal portion of the tubular central stem.

6. The brain probe device of claim 1, further comprising a loop swivel attachment, wherein said plurality of wire loops is operably attached to said distal end of said tubular central stem via said loop swivel attachment.

7. The brain probe device of claim 1, wherein each of the plurality of wire loops is configured to expand out in a half-circle or egg-beater shape.

8. The brain probe device of claim 1, wherein said plurality of wire loops comprises two, three, four, five, or six wire loops.

9. The brain probe device of claim 1 in which the tubular central stem is positionable lengthwise within the probe sleeve to vary an amount by which the plurality of wire loops extend beyond the distal portion of said probe sleeve to control said outward expansion and contraction of said plurality of wire loops.

10. A system comprising:
a) a probe device comprising:
  i) a tubular central stem, wherein said tubular central stem comprises a proximal portion, a distal portion, and a distal end, wherein a plurality of tissue removal openings are formed in said distal portion of said tubular central stem, wherein said tubular central stem includes a rotating side cutter configured to allow cutting of tissue with said plurality of tissue removal openings, and allow aspiration of said tissue through said plurality of tissue removal openings;
  ii) a probe sleeve, wherein said probe sleeve comprises a proximal portion, and a distal portion, wherein said proximal portion encloses most or all of said proximal portion of said tubular central stem, the probe sleeve including an irrigation lumen configured for transferring irrigation fluid to irrigate said tissue in synchrony with aspiration of said tissue;
  iii) at least one wire loop, wherein said at least one wire loop is operably attached to said distal end of said tubular central stem and extends beyond said distal portion of said probe sleeve, the at least one wire loop being configured to be outwardly expanded from said tubular central stem from a contracted configuration to a preset expanded configuration, the probe device being adjustable such that the preset expanded configuration can be selected from a plurality of expanded configurations, each of the plurality of expanded configurations having a different amount of expansion of the at least one wire loop from said tubular central stem beyond which further expansion of the at least one wire loop from the tubular central stem is blocked for the respective preset expanded configuration, and wherein said at least one wire loop is:
  A) configured for cutting the tissue for subsequent removal via the tubular central stem,
  B) configured to be rotated around said distal portion of said tubular central stem and
  C) configured to be outwardly expanded from the contracted configuration to the preset expanded configuration and contracted from the preset expanded configuration to the contracted configuration;
 iv) a loop expander and rotation motor mechanism which is operably linked to said at least one wire loop, the loop expander and rotation mechanism configured to cause rotation of said at least one wire loop around said distal portion of said tubular central stem and the outward expansion of said at least one wire loop from the contracted configuration to the preset expanded configuration, wherein said loop expander and rotation motor mechanism is located in said probe sleeve, the loop expander and rotation motor mechanism being mounted on the proximal portion of the probe sleeve, the tubular central stem proximal portion including a spline-shaped elevator mechanism inside the probe sleeve, and wherein a first gear interconnects the loop expander and rotation motor mechanism and the elevator mechanism to enable rotation of the tubular central stem while permitting movement of the tubular central stem lengthwise within the probe sleeve; and
 v) a rotational cutting motor mechanism attached to said tubular central stem to rotate the rotating side cutter independently of the loop expander and rotation motor mechanism, the rotational cutting motor mechanism including a rotational motor mounted on the proximal portion of the tubular central stem and a second gear interconnecting the rotational motor and the rotating side cutter to rotate the rotating side cutter independently of the loop expander and rotation motor mechanism and movement of the tubular central stem lengthwise within the probe sleeve;
b) a probe actuation subsystem comprising:
 i) an energy generating component coupled to the tubular central stem for energizing the at least one wire loop,
 ii) an irrigation supply component for supplying fluid to the irrigation lumen; and
 iii) a system controller component for selectably actuating the loop expander and rotation motor mechanism.

11. The system of claim 10, wherein said energy generating component comprises a radiofrequency (RF) generating component coupled electrically to the at least one wire loop at the proximal portion of the tubular central stem.

12. The system of claim 10, wherein the system further comprises a cannula sized and shaped so that said probe device can be inserted through said cannula.

13. The system of claim 10, wherein said at least one wire loop has a proximal portion and a distal portion, and wherein said loop expander and rotation motor mechanism is configured to controllably displace said proximal portion of said at least one wire loop distally so as to enable outward expansion of said at least one wire loop from the contracted configuration to the preset expanded configuration.

14. The system of claim 10, further comprising an energy generator connection, wherein said energy generator connection is attached to said probe sleeve.

15. The system of claim 10, further comprising an irrigation fluid input port, wherein said irrigation fluid input port is attached to said probe sleeve and in fluid communication with said irrigation lumen.

16. The system of claim 10, further comprising a vacuum port connection, wherein said vacuum port connection is operatively coupled to the proximal portion of the tubular central stem.

17. The system of claim 10, further comprising a loop swivel attachment, wherein said at least one wire loop is operably attached to said distal end of said tubular central stem via said loop swivel attachment.

18. The system of claim 10, wherein said at least one wire loop expands out in a half-circle or egg-beater shape having a size determined by a distance by which the tubular central stem and said at least one wire loop extends beyond said distal portion of said probe sleeve.

19. The system of claim 10, wherein said at least one wire loop comprises two, three, four, five, or six wire loops.

20. The system of claim 10, wherein said at least one wire loop is configured to outwardly expand away from the tubular central stem, said at least one wire loop having a diameter determined by a radial distance by which the tubular central stem and said at least one wire loop extend beyond said distal portion of said proximal probe sleeve, wherein said at least one wire loop is configured to axially lock relative to the tubular central stem when the rotation of said at least one wire loop about the cannula axis is ceased so as to prevent collapse of remaining tissue in response to severing and aspiration of the tissue of the lesion via the first and second tubes.

* * * * *